United States Patent
Wilhelm et al.

(10) Patent No.: US 10,501,802 B2
(45) Date of Patent: Dec. 10, 2019

(54) BIOMARKERS FOR ACUTE MYELOID LEUKEMIA

(71) Applicants: UNIVERSITE DE MONTREAL, Montreal (CA); UNIVERSITE LAVAL, Quebec (CA)

(72) Inventors: Brian Thomas Wilhelm, Montreal (CA); Frederic Barabe, Quebec (CA)

(73) Assignees: UNIVERSITE DE MONTREAL, Montréal QC (CA); UNIVERSITÉ LAVAL, Québec QC (CA)

( * ) Notice: Subject to any disclaimer, the term of this patent is extended or adjusted under 35 U.S.C. 154(b) by 230 days.

(21) Appl. No.: 14/888,108

(22) PCT Filed: Apr. 30, 2014

(86) PCT No.: PCT/CA2014/050410
§ 371 (c)(1),
(2) Date: Oct. 30, 2015

(87) PCT Pub. No.: WO2014/176696
PCT Pub. Date: Nov. 6, 2014

(65) Prior Publication Data
US 2016/0060709 A1 Mar. 3, 2016

Related U.S. Application Data

(60) Provisional application No. 61/817,616, filed on Apr. 30, 2013.

(51) Int. Cl.
| G01N 33/574 | (2006.01) |
| C07K 16/18 | (2006.01) |
| C07K 16/28 | (2006.01) |
| C07K 16/40 | (2006.01) |
| C12Q 1/6886 | (2018.01) |

(52) U.S. Cl.
CPC ............ *C12Q 1/6886* (2013.01); *C07K 16/18* (2013.01); *C07K 16/2827* (2013.01); *C07K 16/40* (2013.01); *G01N 33/57426* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 9,765,148 B2* | 9/2017 | Silence | C07K 16/2875 |
| 2005/0147612 A1* | 7/2005 | Yayon | C07K 16/2863 424/146.1 |
| 2006/0182743 A1* | 8/2006 | Bilsborough | C07K 14/7155 424/143.1 |
| 2009/0028872 A1* | 1/2009 | Terret | C07K 16/2875 424/156.1 |

FOREIGN PATENT DOCUMENTS

| CA | 2253871 | 11/1997 |
| CA | 2624221 | 5/2007 |
| WO | 03/039443 | 5/2003 |
| WO | PCT/CA2014/050410 | 7/2014 |

OTHER PUBLICATIONS

Gattei et al. (Ann. Hematol. 1998 77:207-210).*
Gura (Science, 1997, 278:1041-1042) (Year: 1997).*
Kaiser (Science, 2006, 313: 1370) (Year: 2006).*
Chames et al. (British J. of Pharmacology, 2009, 157, 220-233) (Year: 2009).*
Almagro & Fransson, Frontiers in Bioscience 2008; 13:1619-33 (Year: 2008).*
Mauvieux et al. "NG2 expression in MLL rearranged acute myeloid leukaemia is restricted to monoblastic cases", British Journal of Haematology, 1999, 107, 674-676.
Majeti, R. "Monoclonal antibody therapy directed against human acute myeloid leukemia stem cells", Oncogene, 2011, 30, 1009-1019.
Database Medline, US National Library of Medicine, Jan. 2001.
Akalin, A. et al. methylKit: a comprehensive R package for the analysis of genome-wide DNA methylation profiles. Genome biology 13, R87, doi:10.1186/gb-2012-13-10-r87 (2012).
Akalin, A. et al. Base-pair resolution DNA methylation sequencing reveals profoundly divergent epigenetic landscapes in acute myeloid leukemia. PLoS genetics 8, e1002781, doi:10.1371/journal.pgen.1002781 (2012).
Atanackovic, D. et al. Expression of cancer-testis antigens as possible targets for antigen-specific immunotherapy in head and neck squamous cell carcinoma. Cancer biology & therapy 5, 1218-1225 (2006).
Balgobind, B. V., Zwaan, C. M., Pieters, R. & Van den Heuvel-Eibrink, M. M. The heterogeneity of pediatric MLL-rearranged acute myeloid leukemia. Leukemia 25, 1239-1248, doi:10.1038/leu.2011.90 (2011).
Barabe, F., Kennedy, J. A., Hope, K. J. & Dick, J. E. Modeling the initiation and progression of human acute leukemia in mice. Science 316, 600-604, doi:10.1126/science.1139851 (2007).
Barretina, J. et al. The Cancer Cell Line Encyclopedia enables predictive modelling of anticancer drug sensitivity. Nature 483, 603-607, doi:10.1038/nature11003 (2012).
Basson, M. A. et al. Sprouty1 is a critical regulator of GDNF/RET-mediated kidney induction. Developmental cell 8, 229-239, doi:10.1016/j.devcel.2004.12.004 (2005).

(Continued)

*Primary Examiner* — Peter J Reddig
(74) *Attorney, Agent, or Firm* — Norton Rose Fulbright

(57) ABSTRACT

Methods for the diagnosis of leukemias, and more specifically AML, such as MLL-AF9 AML, in a subject, based on the assessment of the expression or activity of one or more of the genes listed in Tables 1 and 2 are disclosed. The use of antibodies or antigen-binding fragments thereof that bind to one or more of proteins showing preferential expression at the cell surface of AML leukemic cells for treating AML is also disclosed.

3 Claims, 8 Drawing Sheets

(56) References Cited

OTHER PUBLICATIONS

Cancer Genome Atlas Research, N. Genomic and epigenomic landscapes of adult de novo acute myeloid leukemia. The New England journal of medicine 368, 2059-2074, doi:10.1056/NEJMoa1301689 (2013).
Challen, G. A. et al. Dnmt3a is essential for hematopoietic stem cell differentiation. Nature genetics 44, 23-31, doi:10.1038/ng.1009 (2012).
Da Huang, W., Sherman, B. T. & Lempicki, R. A. Systematic and integrative analysis of large gene lists using David bioinformatics resources. Nature protocols 4, 44-57, doi:10.1038/nprot.2008.211 (2009).
Dobbins, S. E. et al. The silent mutational landscape of infant MLL-AF4 pro-B acute lymphoblastic leukemia. Genes, chromosomes & cancer 52, 954-960, doi:10.1002/gcc.22090 (2013).
Figlioli, G., Landi, S., Romei, C., Elisei, R. & Gemignani, F. Medullary thyroid carcinoma (MTC) and RET proto-oncogene: mutation spectrum in the familial cases and a meta-analysis of studies on the sporadic form. Mutation research 752, 36-44, doi:10.1016/j.mrrev.2012.09.002 (2013).
Fonseca-Pereira, D. et al. The neurotrophic factor receptor RET drives haematopoietic stem cell survival and function. Nature 514, 98-101, doi:10.1038/nature13498 (2014).
Forster, A. et al. Engineering de novo reciprocal chromosomal translocations associated with MLL to replicate primary events of human cancer. Cancer cell 3, 449-458 (2003).
Gattei, V. et al. Expression of the RET receptor tyrosine kinase and GDNFR-alpha in normal and leukemic human hematopoietic cells and stromal cells of the bone marrow microenvironment. Blood 89, 2925-2937 (1997).
Greaves, M. F., Maia, A. T., Wiemels, J. L. & Ford, A. M. Leukemia in twins: lessons in natural history. Blood 102, 2321-2333, doi:10.1182/blood-2002-12-3817 (2003).
Grimwade, D. et al. Refinement of cytogenetic classification in acute myeloid leukemia: determination of prognostic significance of rare recurring chromosomal abnormalities among 5876 younger adult patients treated in the United Kingdom Medical Research Council trials. Blood 116, 354-365, doi:10.1182/blood-2009-11-254441 (2010).
Grossmann, V. et al. High incidence of RAS signalling pathway mutations in MLL-rearranged acute myeloid leukemia. Leukemia 27, 1933-1936, doi:10.1038/leu.2013.90 (2013).
Ho, P. A. et al. Leukemic mutations in the methylation-associated genes DNMT3A and IDH2 are rare events in pediatric AML: a report from the Children's Oncology Group. Pediatr Blood Cancer 57, 204-209, doi:10.1002/pbc.23179 (2011).
Horton, S. J. et al. MLL-AF9-mediated immortalization of human hematopoietic cells along different lineages changes during ontogeny. Leukemia 27, 1116-1126, doi:10.1038/leu.2012.343 (2013).
Ibanez, C. F. Structure and physiology of the RET receptor tyrosine kinase. Cold Spring Harbor perspectives in biology 5, doi:10.1101/cshperspect.a009134 (2013).
Jiang, X. et al., "miR-495 is a tumor-supressor microRNA down-regulated in MLL-rearranged leukemia", PNAS, Nov. 20, 2012 (Nov. 20, 2012), vol. 109, No. 47, pp. 19397-19402.
Kandoth, C. et al. Mutational landscape and significance across 12 major cancer types. Nature 502, 333-339, doi:10.1038/nature12634 (2013).
Krueger, F. & Andrews, S. R. Bismark: a flexible aligner and methylation caller for Bisulfite-Seq applications. Bioinformatics 27, 1571-1572, doi:10.1093/bioinformatics/btr167 (2011).
Lavallee, V. P. et al. The transcriptomic landscape and directed chemical interrogation of MLL-rearranged acute myeloid leukemias. Nature genetics, 47(9), 1030-1037, doi:10.1038/ng.3371 (2015).
Lee, 1. et al., "A comparison of gene expression profiles between primary human AMLcell line", Genes Genet. Syst., 2008, vol. 83, pp. 339-345.
Ley, T. J. et al. DNMT3A mutations in acute myeloid leukemia. The New England journal of medicine 363, 2424-2433, doi:10.1056/NEJMoa1005143 (2010).
Lister, R. et al. Human DNA methylomes at base resolution show widespread epigenomic differences. Nature 462, 315-322, doi:10.1038/nature08514 (2009).
Mansky, L. M. Retrovirus mutation rates and their role in genetic variation. The Journal of general virology 79 ( Pt 6), 1337-1345 (1998).
Miller, P. G. et al. In Vivo RNAi screening identifies a leukemia-specific dependence on integrin beta 3 signaling. Cancer cell 24, 45-58, doi:10.1016/j.ccr.2013.05.004 (2013).
Morandi, A. et al. GDNF-RET signaling in ER-positive breast cancers is a key determinant of response and resistance to aromatase inhibitors. Cancer research 73, 3783-3795, doi:10.1158/0008-5472.CAN-12-4265 (2013).
Mostafavi, S., Ray, D., Warde-Farley, D., Grouios, C. & Morris, Q. GeneMANIA: a real-time multiple association network integration algorithm for predicting gene function. Genome biology 9 Suppl 1, S4, doi:10.1186/gb-2008-9-s1-s4 (2008).
Mulligan, L. M. RET revisited: expanding the oncogenic portfolio. Nature reviews. Cancer 14, 173-186, doi:10.1038/nrc3680 (2014).
Mullighan, C. G. et al. JAK mutations in high-risk childhood acute lymphoblastic leukemia. Proceedings of the National Academy of Sciences of the United States of America 106, 9414-9418, doi:10.1073/pnas.0811761106 (2009).
Pennacchio, L. A. et al. In vivo enhancer analysis of human conserved non-coding sequences. Nature 444, 499-502, doi:10.1038/nature05295 (2006).
Ponder, B. A. The phenotypes associated with ret mutations in the multiple endocrine neoplasia type 2 syndrome. Cancer research 59, 1736s-1741s; discussion 1742s (1999).
Ross, M. E. et al. Gene expression profiling of pediatric acute myelogenous leukemia. Blood 104, 3679-3687, doi:10.1182/blood-2004-03-1154 (2004).
Salvatore, G. et al. Generation and characterization of novel monoclonal antibodies to the Ret receptor tyrosine kinase. Biochemical and biophysical research communications 294, 813-817, doi:10.1016/S0006-291X(02)00560-0 (2002).
Santoro, M. et al. Ret oncogene activation in human thyroid neoplasms is restricted to the papillary cancer subtype. The Journal of clinical investigation 89, 1517-1522, doi:10.1172/JCI115743 (1992).
Schoch, C. et al. AML with 11q23/MLL abnormalities as defined by the WHO classification: incidence, partner chromosomes, FAB subtype, age distribution, and prognostic impact in an unselected series of 1897 cytogenetically analyzed AML cases. Blood 102, 2395-2402, doi:10.1182/blood-2003-02-0434 (2003).
Takeda, A., Goolsby, C. & Yaseen, N. R. NUP98-HOXA9 induces long-term proliferation and blocks differentiation of primary human CD34+ hematopoietic cells. Cancer research 66, 6628-6637 (2006).
Vardiman, J. W. et al. The 2008 revision of the World Health Organization (WHO) classification of myeloid neoplasms and acute leukemia: rationale and important changes. Blood 114, 937-951, doi:10.1182/blood-2009-03-209262 (2009).
Valk, P. J. et al. Prognostically useful gene-expression profiles in acute myeloid leukemia. The New England journal of medicine 350, 1617-1628, doi:10.1056/NEJMoa040465 (2004).
Wang, H. Q., Tuominen, L. K. & Tsai, C. J. Slim: a sliding linear model for estimating the proportion of true null hypotheses in datasets with dependence structures. Bioinformatics 27, 225-231, doi:10.1093/bioinformatics/btq650 (2011).
Warde-Farley, D. et al. The GeneMANIA prediction server: biological network integration for gene prioritization and predicting gene function. Nucleic Acids Res 38, W214-220, doi:gkq537 [pii]10.1093/nar/gkq537 (2010).
Watkins, N. A. et al. A HaemAtlas: characterizing gene expression in differentiated human blood cells. Blood 113, e1-9, doi:10.1182/blood-2008-06-162958 (2009).
Wei, J. et al. Microenvironment determines lineage fate in a human model of MLL-AF9 leukemia. Cancer cell 13, 483-495, doi:10.1016/j.ccr.2008.04.020 (2008).

(56) References Cited

OTHER PUBLICATIONS

Xiang, Z. et al. Identification of somatic JAK1 mutations in patients with acute myeloid leukemia. Blood 111, 4809-4812, doi:10.1182/blood-2007-05-090308 (2008).

Zang, X. et al. B7-H3 and B7x are highly expressed in human prostate cancer and associated with disease spread and poor outcome. Proceedings of the National Academy of Sciences of the United States of America 104, 19458-19463, doi:10.1073/pnas.0709802104 (2007).

Zuber, J. et al. Mouse models of human AML accurately predict chemotherapy response. Genes & development 23, 877-889, doi:10.1101/gad.1771409 (2009).

Schoch et al. "AML with 11q23/MLL abnormalities as defined by the WHO classification: incidence, partner chromosomes, FAB subtype, age distribution, and prognostic impact in an unselected series of 1897 cytogenetically analyzed AML cases", Blood, vol. 102, No. 7, pp. 2395-2402.

Ommen et al. "Relapse Kinetics in acute myeloid leukaemias with MLL translocations or partial tandem duplications within the MLL gene", British Journal of Haematology, 2014, 165, 618-628.

Bullinger et al. "Use of Gene-Expression Profiling to Identify Prognostic Subclasses in Adult Acute Myeloid Leukemia", The New England Journal of Medicine, vol. 350, No. 16, 2004, 1605-1616.

Asano et al. "Complete molecular remission in refactory acute myeloid leukemia with MLL/AF9 treated with gemtuzumab ozogamicin", Leukemia Research, vol. 34, No. 7m 2010, pp. e-125-e153.

Salvatore et al.,"Generation and characterization of novel monoclonal antibodies to the Ret receptor tyrosine kinase", 2002, Biochem Biophys Res Commun, 294, 21: 813-817.

Yano et al., "improved Gene Transfer to Neuroblastoma Cells by a Monoclonal Antibody Targeting RET, a Receptor Tyrosine Kinase", Human Gene Therapy, 11: 995-1004 .2000.

Tam et al., "Ret Protein in the Human Fetal Rectum", J Pediatr Surg, vol. 31: 568-571, 1996.

Mireia et al. "Gene expression signature of acute myeloid leukemia (AML) with T(8:16)(P11;P13) and MYST-3-CREBBP rearrangement: A microarray study validated by multiple real-time PCR". Blood, vol. 106, No. 11, Part 1, Nov. 2005.

Fontana et al. "c-Jun in Schwann cells promotes axonal regeneration and motoneuron survival via paracrine signaling", J. Cell Biol. vol. 198, No. 1, 127-141.

Licciulli et al. "FRAX597, a Small Molecule Inhibitor of the p21-activated Kinases, Inhibits Tumorigenesis of Neurofibromatosis Type 2 (NF2)-associated Schwannomas", Journal of Biological Chemistry, vol. 288, No. 40, pp. 29105-29114. 2013.

\* cited by examiner cDNA: KG1a, 30 cycles cDNA: KG1a, 35 cycles

BIOMARKERS FOR ACUTE MYELOID LEUKEMIA

CROSS REFERENCE TO RELATED APPLICATIONS

The present application claims the benefit of U.S. Provisional Application Ser. No. 61/817,616 filed on Apr. 30, 2013, which is incorporated herein by reference in its entirety.

TECHNICAL FIELD

The present invention generally relates to leukemia, and more specifically to the diagnosis and treatment of acute myeloid leukemia (AML).

BACKGROUND ART

Leukemias arise when stem/hematopoietic progenitor cells acquire mutations that enable them to escape control mechanisms regulating proliferation and which disable the cells' ability to differentiate. Two subtypes exist which are defined by the cells involved: lymphoid cells (Acute Lymphoid Leukemia; ALL) or myeloid cells (Acute Myeloid Leukemia; AML). Despite many years of research, a comprehensive understanding of all of the genetic causes of leukemia has not yet been generated. One class of leukemias of clinical interest are those which involve translocations of the mixed-lineage leukemia (MLL) gene. MLL was cloned in 1992 from the t(11;19) (11q23;19p13) chromosomal translocation that is recurrently associated with both myelomonocytic AML and ALL. MLL is a large gene (~90 kb) and its 11.9 kb mRNA encodes a protein of 3968 amino acids with a very complex structure. MLL is a key regulator of hematopoiesis and is also important in embryogenesis for its positive regulation of homeobox HOX gene expression. To date, more than 50 different translocations involving MLL have been identified in acute human leukemias. The most common MLL fusion partners in AMLs are AF9 t(9:11), AF10, AF6 and ELL. MLL fusion genes are also identified in more than 30% of therapy-related leukemias, typically after topoisomerase II inhibitors or alkylating agent therapies. Generally, 11q23 translocations confer a poor prognosis similar to unfavorable prognostic subgroups of ALL and AML.

The present description refers to a number of documents, the content of which is herein incorporated by reference in their entirety.

SUMMARY OF THE INVENTION

The present invention provides methods for the diagnosis, assessment and treatment of AML in a subject based on the assessment and modulation of the expression or activity of one or more of the genes listed in Tables 1 and 2.

The present invention provides the following items 1 to 35:

1. A method for determining whether a subject suffers from MLL-AF9 acute myeloid leukemia (AML), said method comprising (i) measuring the expression of one or more of the genes listed in Table 7 in a sample from the subject;

TABLE 7

| | | |
|---|---|---|
| SYT17 | KIF26B | BCL2L10 |
| DES | NAV3 | LOC100289656 |
| IL31RA | ITGA7 | KCNN2 |
| CABP4 | NXF3 | AGT |
| LPL | PDZD7 | LOC728606 |
| CCL23 | CLSTN2 | SAGE1 |
| TRPM4 | PHACTR3 | ARTN |
| MT1G | SCUBE1 | TGM5 |
| RET | SLC22A20 | PITX1 |
| C17orf55 | GIPR | TMEM105 |
| FAM70A | DYSFIP1 | CD276 |
| RUFY4 | DEFB1 | CCDC144NL |
| NRG4 | METTL7B | HOXA11 |

(ii) comparing said expression to a control expression; and
(iii) determining whether the subject suffers from AML based on said comparing.

2. A method for determining whether a subject suffers from MLL-AF9 leukemia, said method comprising (i) measuring the expression of one or more of the genes listed in Table 8 in a sample from the subject;

TABLE 8

| | | |
|---|---|---|
| CD70 | CTGF | GAS2L3 |
| LAMP5 | ECM1 | SERINC2 |
| THBS4 | CDKN2A | GPM6B |
| LOC84989 | PENK | PHLDA3 |

(ii) comparing said expression to a control expression; and
(iii) determining whether the subject suffers from AML based on said comparing.

3. The method of item 1 or 2, wherein said method is for assessing minimal residual disease (MRD) in said patient.

4. The method of any one of items 1-3, wherein said sample comprises bone marrow cells.

5. The method of any one of items 1-4, wherein said control expression is an expression measured in a normal stem cell and/or hematopoietic progenitor cell sample.

6. The method of any one of items 1-5, wherein said expression is measured at the nucleic acid level.

7. The method of item 6, wherein said method comprises obtaining cDNA corresponding to said one or more genes from said sample and measuring the level of said cDNA.

8. The method of item 7, wherein said method further comprises performing an amplification reaction on said cDNA.

9. The method of item 8, wherein said amplification reaction comprises a polymerase chain reaction (PCR).

10. The method of any one of items 7-9, wherein the level of said cDNA is measured by quantitative PCR.

11. The method of any one of items 7-9, wherein the level of said cDNA is measured by RNA sequencing (RNA-seq).

12. The method of any one of items 1-5, wherein said expression is measured at the protein level.

13. The method of item 12, wherein said method comprises contacting a protein encoded by said one or more of the genes with an antibody specifically recognizing said protein.

14. The method of any one of items 1 to 3, wherein said sample is a blood-derived sample and said method comprises measuring the level of one or more of the following proteins in said sample: SCUBE1, LPL, CCL23, DEFB1, AGT, ARTN, THBS4, CTGF, ECM1 and/or PENK.

15. A method for treating acute myeloid leukemia (AML) in a subject, said method comprising administering to said subject an effective amount of an antibody that binds to one or more of the following proteins: SYT17, FAM70A, NRG4, CLSTN2, SLC22A20, GIPR, KCNN2, TMEM105, CD276, IL31RA, TRPM4, RET, ITGA7, CD70, LAMP5, SERINC2, GPM6B and/or SCUBE1, or an antigen-binding fragment thereof.

16. The method of item 15, wherein said antibody or antigen-binding fragment thereof binds to SCUBE1.

17. The method of item 15, wherein said antibody or antigen-binding fragment thereof binds to RET.

18. The method of item 15, wherein said antibody or antigen-binding fragment thereof binds to CD276.

19. The method of any one of items 15-18, wherein said antibody is a monoclonal antibody.

20. The method of any one of items 15-19, wherein said AML involves translocation of the mixed-lineage leukemia (MLL) gene.

21. The method of item 20, wherein said AML is MLL-AF9.

22. Use of an antibody that binds to one or more of the following proteins: SYT17, FAM70A, NRG4, CLSTN2, SLC22A20, GIPR, KCNN2, TMEM105, CD276, IL31RA, TRPM4, RET, ITGA7, CD70, LAMP5, SERINC2, GPM6B and/or SCUBE1, or an antigen-binding fragment thereof, for treating acute myeloid leukemia (AML) in a subject.

23. Use of an antibody that binds to one or more of the following proteins: SYT17, FAM70A, NRG4, CLSTN2, SLC22A20, GIPR, KCNN2, TMEM105, CD276, IL31RA, TRPM4, RET, ITGA7, CD70, LAMP5, SERINC2, GPM6B and/or SCUBE1, or an antigen-binding fragment thereof, for the preparation of a medicament for treating acute myeloid leukemia (AML) in a subject.

24. The use of item 22 or 23, wherein said antibody or antigen-binding fragment thereof binds to SCUBE1.

25. The use of item 22 or 23, wherein said antibody or antigen-binding fragment thereof binds to RET.

26. The use of item 22 or 23, wherein said antibody or antigen-binding fragment thereof binds to CD276.

27. The use of any one of items 22-26, wherein said antibody is a monoclonal antibody.

28. The use of any one of items 22-27, wherein said AML involves translocation of the mixed-lineage leukemia (MLL) gene.

29. The use of item 28, wherein said AML is MLL-AF9.

30. A method for detecting MLL-AF9 leukemia cells in a sample, said method comprising contacting said sample with an antibody that binds to one or more of the following proteins: SYT17, FAM70A, NRG4, CLSTN2, SLC22A20, GIPR, KCNN2, TMEM105, CD276, IL31RA, TRPM4, RET, ITGA7, CD70, LAMP5, SERINC2, GPM6B and/or SCUBE1, or an antigen-binding fragment thereof, wherein said antibody or antigen-binding fragment thereof is labelled.

31. A method for detecting MLL-AF9 leukemia cells in a subject, said method comprising administering to said subject an antibody that binds to one or more of the following proteins: SYT17, FAM70A, NRG4, CLSTN2, SLC22A20, GIPR, KCNN2, TMEM105, CD276, IL31RA, TRPM4, RET, ITGA7, CD70, LAMP5, SERINC2, GPM6B and/or SCUBE1, or an antigen-binding fragment thereof.

32. The method of item 30 or 31, wherein said antibody or antigen-binding fragment thereof is labelled.

33. The method of item 32, wherein said antibody or antigen-binding fragment thereof is labelled with a fluorescent moiety.

34. Use of an antibody that binds to one or more of the following proteins: SYT17, FAM70A, NRG4, CLSTN2, SLC22A20, GIPR, KCNN2, TMEM105, CD276, IL31RA, TRPM4, RET, ITGA7, CD70, LAMP5, SERINC2, GPM6B and/or SCUBE1, or an antigen-binding fragment thereof, for detecting MLL-AF9 leukemia cells in a subject.

35. The use of item 34, wherein said antibody or antigen-binding fragment thereof is labelled.

36. The use of item 35, wherein said antibody or antigen-binding fragment thereof is labelled with a fluorescent moiety.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 2A shows the distribution of gene expression values between two AMLs derived from independent cord blood donors.

FIG. 4B=CCL23; FIG. 4C=METTL7B; FIG. 4D=DYSFIP1). Boxplots of gene expression (log 2 RPKM) levels in normal tissues (two left boxes), model leukemia populations (four middle boxes) and patient samples (two right boxes) demonstrate expression specific to MA9-AML for candidates. Dashed line at 0 represents the threshold for a gene to be considered "expressed" (RPKM>1). High outliers in TCGA data generally represent the patients in this data set with MLL translocations;

FIG. 7A confirms that the candidate gene AGT can be detected in the MA9 cell line THP-1 (T), but not in KG1a cells (K), peripheral blood from healthy donor (D) or in control without template (−).

FIGS. 8A and B show KG1a cDNA used as input for RT-PCR reactions using primers against 7 candidate genes (including 2 different primer pairs against RET). FIGS. 8C and D show the same primer pairs used under identical RT-PCR conditions but with THP-1 cDNA used as input. Resulting PCR products using either 30 (FIGS. 8A and C) or 35 (FIGS. 8B and D) cycles are shown after gel electrophoresis. The results demonstrate that the candidate genes can be used to distinguish cells containing an MLL-AF9 translocation (THP-1) from those that do not contain an MLL-AF9 translocation (KG1a). The lack of specific amplification products in non-MLL-AF9 cells after 35 cycles for most of these genes demonstrates that these candidate genes have a high level of sensitivity. The bands seen with RET primer pairs 4 and 5 (RET-4 and RET-5) likely result from non-specific amplification of related gene sequences, since a smaller RT-PCR product for RET using different primers cannot be generated from KG1a cDNA (FIG. 7B, left panel).

FIG. 9A demonstrates that some of the candidates identified as being expressed in MLL-AF9 AML are expressed in other leukemias.

DISCLOSURE OF INVENTION

Figure 1:
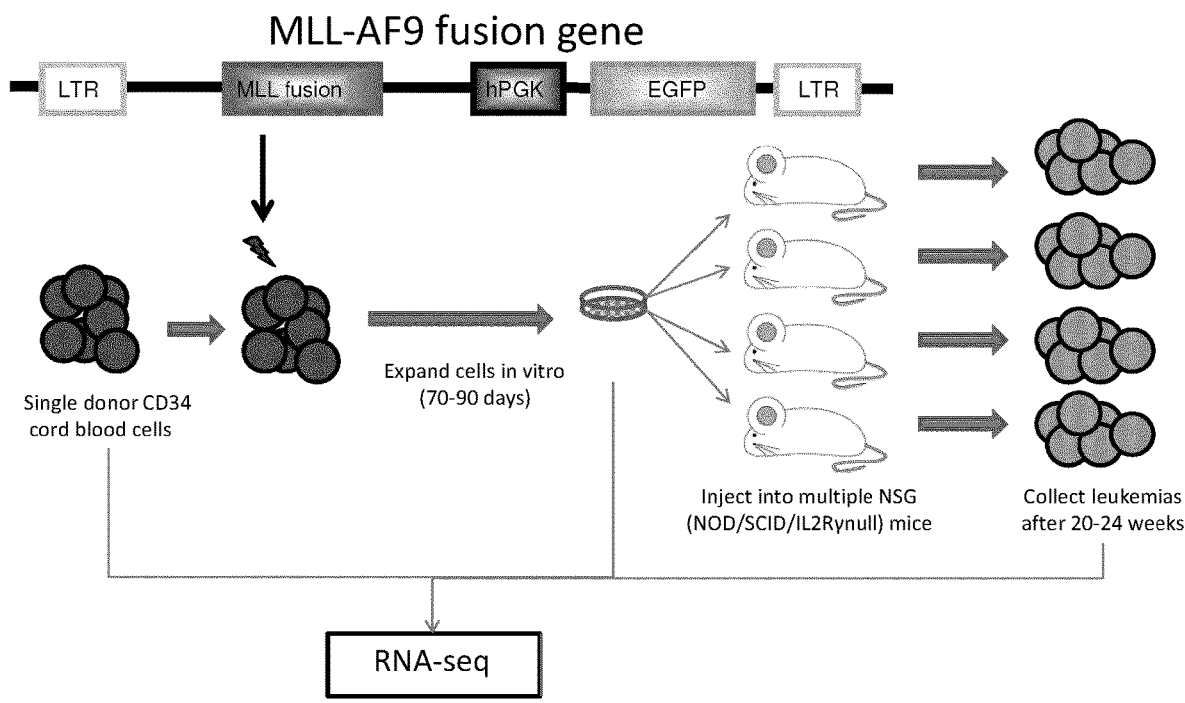
FIG. 1 shows the experimental method for generating single donor model leukemias and generating RNA-seq data for each developmental stage. $CD34^+$ cells are positively selected from single healthy cord blood (CB) donors. To begin with, two $1 \times 10^5$ cell aliquots are kept for exome sequencing and RNA-seq and approximately $1 \times 10^6$ cells are transduced with a retrovirus expressing the human MLL-AF9 cDNA and GFP. Transduced cells are expanded for 30 days before injection into NSG mice and are also grown in vitro for an additional 50-60 days. Mice develop leukemias typically after 20-24 weeks and are sacrificed to collect bone marrow. CB cells ($1 \times 10^5$), MA9 expanded cells ($1 \times 10^6$) and blast cells from each leukemia ($1 \times 10^6$) are collected and used for RNA-seq and exome sequencing.

Next generation sequencing of the tumor transcriptomes (RNA-seq) of pediatric AML patients can provide information regarding mutations and gene expression present in the disease. While informative, it was found that the complex genetic heterogeneity of the individual patients can be confounding when analysing the genetic determinates of the leukemia. A unique model system which combines human cord blood cells from single donors with the human MLL-AF9 fusion gene was used to generate multiple independent leukemias in a single genetic background. Both AML and B-cell ALL (B-ALL) can be generated using this approach and because RNA-seq can be performed on the original cord blood cells, the MLL-AF9 expanded cells, as well as the resulting leukemias, it is possible to "track" gene expression changes during the evolution of the tumor. This is impossible using actual patient samples since they are only available once the leukemia has fully developed and the patient presents clinically. Thus, this novel approach has allowed us to study gene expression during MLL-AF9 leukemia development. We have used this approach for several cord blood donors and generated multiple leukemias (both AML and B-ALL) and compared RNA-seq data from these samples, along with several t(9:11) pediatric AML samples, to publically available or published RNA-seq for normal tissues, normal blood cells or a variety of patient acute myeloid leukemias and AML cell lines. These analyses have revealed a number of genes whose expression is absent in normal tissues/blood cells and in most AML samples but high in both MLL-AF9 model leukemias and patient samples.

There are several potential uses for the genes identified through the analysis described herein. The first potential use is for the diagnostic testing of patient leukemia in a clinical setting. Currently, AML patients who require clinical diagnosis must undergo testing in order to identify their sub-type of leukemia with some precision. The initial classification is typically made using flow cytometry in order to differentiate myeloid and lymphoid leukemias. Several of the biomarkers we have identified could easily be adapted as additional flow cytometry-based tests to define the leukemia subclass with greater precision and to help guide eventual cytogenetic testing. Other targets identified could be used as ELISA-based assays for alternative diagnostic methods which would be rapid and inexpensive and robust. Given their specific association with AML, these same biomarkers may also likely have prognostic value since their expression within individual patients and model leukemias is variable and may correlate with the future response to treatment. This can be validated by correlating clinical data associated with the patient outcomes to gene expression level, or through in vitro assays using the model leukemias which can be grown in culture for extended periods of time. Thirdly, because many of the biomarkers are highly expressed in leukemias, they may have utility in monitoring minimal residual disease which in AML is linked to patient relapse. Important to this potential function is that the biomarkers should not be expressed in normal blood cells, which the expression data for normal blood cells strongly suggests is the case for these genes. Lastly, because a number of these genes are predicted or demonstrated to be expressed on the cell surface, they could be used to directly target leukemia cells using immunological-based approaches (e.g., antibodies such as humanized antibodies) or through other suitable ligands.

Diagnosis of AML

The present invention provides a method for determining whether a subject suffers from acute myeloid leukemia (AML), said method comprising (i) measuring the expression of one or more of the genes listed in Table 1 or Table 2 in a sample from the subject; (ii) comparing said expression to a control expression; and (iii) determining whether the subject suffers from AML based on said comparing.

The present invention provides a method for determining the likelihood that a subject suffers from acute myeloid leukemia (AML), said method comprising (i) measuring the expression of one or more of the genes listed in Table 1 or Table 2 in a sample from the subject; (ii) comparing said expression to a control expression; and (iii) determining the likelihood that the subject suffers from AML based on said comparing.

The present invention also provides a method for determining whether a subject suffers from MLL-AF9 AML, said method comprising (i) measuring the expression of one or more of the genes listed in Table 1 in a sample from the subject; (ii) comparing said expression to a control expression; and (iii) determining whether the subject suffers from AML based on said comparing.

The present invention also provides a method for determining the likelihood that a subject suffers from MLL-AF9 AML, said method comprising (i) measuring the expression of one or more of the genes listed in Table 1 in a sample from the subject; (ii) comparing said expression to a control expression; and (iii) determining the likelihood that the subject suffers from AML based on said comparing.

The present invention also provides a method for determining whether a subject suffers from MLL-AF9 leukemias, said method comprising (i) measuring the expression of one or more of the genes listed in Table 2 in a sample from the subject; (ii) comparing said expression to a control expression; and (iii) determining whether the subject suffers from AML based on said comparing.

The present invention also provides a method for determining the likelihood that a subject suffers from MLL-AF9 leukemias, said method comprising (i) measuring the expression of one or more of the genes listed in Table 2 in a sample from the subject; (ii) comparing said expression to a control expression; and (iii) determining the likelihood that the subject suffers from AML based on said comparing.

TABLE 1

List of MLL-AF9 AML candidate genes based on gene expression values

| Gene | Average Mono | Average CD34 | Average MA9 | Average mBALL |
|---|---|---|---|---|
| SYT17 | 0.40 | 0.11 | 0.53 | 0.26 |
| DES | 0.58 | 0.18 | 0.27 | 0.20 |
| IL31RA | 0.28 | 0.03 | 1.17 | 0.03 |
| CABP4 | 0.32 | 0.16 | 0.04 | 0.25 |
| LPL | 0.07 | 0.14 | 38.28 | 0.51 |
| CCL23 | 0.18 | 0.71 | 114.48 | 0.84 |
| TRPM4 | 0.61 | 0.62 | 2.04 | 0.19 |
| MT1G | 0.05 | 0.24 | 4.23 | 0.68 |
| RET | 0.08 | 0.22 | 0.61 | 0.06 |
| C17orf55 | 0.36 | 0.03 | 0.21 | 0.03 |
| FAM70A | 0.27 | 0.24 | 2.71 | 0.25 |
| RUFY4 | 0.51 | 0.18 | 0.13 | 0.08 |
| NRG4 | 0.13 | 0.55 | 0.47 | 0.34 |
| KIF26B | 0.12 | 0.19 | 0.39 | 0.80 |
| NAV3 | 0.01 | 0.01 | 1.77 | 0.07 |
| ITGA7 | 0.40 | 0.53 | 2.53 | 0.47 |
| NXF3 | 0.05 | 0.17 | 1.85 | 0.04 |
| PDZD7 | 0.07 | 0.12 | 0.36 | 0.70 |
| CLSTN2 | 0.00 | 0.03 | 0.00 | 0.04 |
| PHACTR3 | 0.02 | 0.01 | 1.03 | 0.51 |
| SCUBE1 | 0.03 | 0.18 | 23.64 | 0.16 |
| SLC22A20 | 0.12 | 0.53 | 1.87 | 0.32 |
| GIPR | 0.32 | 0.03 | 9.99 | 0.81 |
| DYSFIP1 | 0.40 | 0.75 | 6.68 | 0.47 |
| DEFB1 | 0.36 | 0.20 | 6.94 | 0.10 |
| METTL7B | 0.10 | 0.52 | 2.00 | 0.13 |
| BCL2L10 | 0.18 | 0.98 | 0.23 | 0.13 |
| LOC100289656 | 0.01 | 0.01 | 1.01 | 0.07 |
| KCNN2 | 0.00 | 0.00 | 0.02 | 0.02 |
| AGT | 0.05 | 0.06 | 0.87 | 0.04 |
| LOC728606 | 0.01 | 0.09 | 0.84 | 0.05 |
| SAGE1 | 0.01 | 0.11 | 0.01 | 0.02 |
| ARTN | 0.05 | 0.48 | 0.22 | 0.36 |
| TGM5 | 0.01 | 0.13 | 1.39 | 0.10 |
| PITX1 | 0.00 | 0.01 | 0.15 | 0.08 |
| TMEM105 | 0.02 | 0.01 | 0.01 | 0.03 |
| CD276 | 0.03 | 0.58 | 13.40 | 0.10 |
| CCDC144NL | 0.01 | 0.02 | 0.00 | 0.00 |
| HOXA11 | 0.01 | 0.18 | 2.92 | 0.31 |

| Gene | Average mAML | Median pAML | Average TCGA | Median TCGA | BM-WBC |
|---|---|---|---|---|---|
| SYT17 | 4.15 | 5.71 | 0.77 | 0.16 | 0.97 |
| DES | 12.13 | 3.56 | 0.62 | 0.07 | 0.81 |
| IL31RA | 21.75 | 4.84 | 0.65 | 0.10 | 0.40 |
| CABP4 | 4.02 | 3.85 | 0.50 | 0.27 | 0.38 |
| LPL | 47.52 | 3.47 | 3.46 | 0.79 | 0.35 |
| CCL23 | 73.44 | 98.77 | 10.54 | 2.35 | 0.30 |
| TRPM4 | 24.96 | 34.36 | 2.25 | 0.35 | 0.25 |
| MT1G | 3.79 | 30.69 | 1.90 | 0.15 | 0.25 |
| RET | 21.18 | 11.15 | 1.45 | 0.48 | 0.17 |
| C17orf55 | 12.47 | 13.50 | 2.36 | 0.36 | 0.17 |
| FAM70A | 3.64 | 4.42 | 0.54 | 0.33 | 0.12 |
| RUFY4 | 6.19 | 4.07 | 0.63 | 0.20 | 0.11 |
| NRG4 | 5.35 | 7.13 | 6.45 | 3.60 | 0.09 |
| KIF26B | 9.93 | 7.83 | 2.40 | 1.25 | 0.07 |
| NAV3 | 7.47 | 3.48 | 1.28 | 0.13 | 0.06 |
| ITGA7 | 19.31 | 14.81 | 4.10 | 1.67 | 0.05 |
| NXF3 | 6.13 | 3.09 | 6.76 | 2.01 | 0.04 |
| PDZD7 | 5.30 | 4.46 | 1.15 | 0.70 | 0.03 |
| CLSTN2 | 41.73 | 7.68 | 1.28 | 0.08 | 0.02 |
| PHACTR3 | 26.56 | 25.25 | 1.67 | 0.06 | 0.02 |
| SCUBE1 | 56.15 | 36.00 | 5.77 | 1.10 | 0.02 |
| SLC22A20 | 3.69 | 5.12 | 3.04 | 1.86 | 0.01 |
| GIPR | 4.10 | 8.90 | 0.70 | 0.29 | 0.00 |
| DYSFIP1 | 100.45 | 181.51 | 8.05 | 1.26 | 0.00 |
| DEFB1 | 58.35 | 82.21 | 19.27 | 0.93 | 0.00 |
| METTL7B | 12.74 | 20.45 | 10.39 | 3.78 | 0.00 |
| BCL2L10 | 5.35 | 17.41 | 1.57 | 0.22 | 0.00 |
| LOC100289656 | 4.60 | 11.46 | NA | NA | 0.00 |
| KCNN2 | 3.38 | 10.87 | 0.31 | 0.00 | 0.00 |
| AGT | 26.82 | 10.13 | 0.71 | 0.07 | 0.00 |
| LOC728606 | 5.30 | 9.87 | NA | NA | 0.00 |
| SAGE1 | 6.69 | 8.59 | 1.25 | 0.00 | 0.00 |
| ARTN | 9.18 | 8.46 | 5.21 | 2.24 | 0.00 |
| TGM5 | 6.06 | 8.02 | 1.53 | 0.19 | 0.00 |
| PITX1 | 6.20 | 7.91 | 1.71 | 0.03 | 0.00 |
| TMEM105 | 10.22 | 4.39 | 1.18 | 0.17 | 0.00 |
| CD276 | 5.79 | 3.75 | 1.74 | 0.59 | 0.00 |

TABLE 1-continued

List of MLL-AF9 AML candidate genes based on gene expression values

| | | | | | |
|---|---|---|---|---|---|
| CCDC144NL | 3.47 | 3.73 | 0.25 | 0.00 | 0.00 |
| HOXA11 | 32.00 | 3.43 | 1.67 | 0.05 | 0.00 |

Average normalized gene expression values (Reads Per Kilobase pair of gene model per Million reads sequenced; RPKM) for 39 candidate genes are shown with RNA-seq data from: healthy donor monocytes (n = 2), CD34+ cells (n = 5), CD34+ cells after MA9 transduction (MA9, n = 3), model B-ALL (mBALL, n = 7) and AML (mAML, n = 9), pediatric MA9 AML patients (pAML, median shown, n = 3), adult AML from TCGA (average and median RPKM shown, n = 184) and in public RNA-seq data (Bodymap2 project) from purified white blood cells (BMWBC). Candidate genes in this table were specifically selected to have clear expression (RPKM >3) in model and pediatric AML samples but no expression (RPKM <1) in normal monocytes, CD34+ cells and model BALL cells.

TABLE 2

List of MLL-AF9 leukemia candidate genes based on gene expression values.

| Gene | Median pAML | Average Mono | Average CD34 | Average MA9 |
|---|---|---|---|---|
| CD70 | 47.49 | 0.07 | 0.88 | 4.26 |
| LAMP5 | 113.97 | 0.74 | 0.28 | 1.00 |
| THBS4 | 9.98 | 0.45 | 0.20 | 1.63 |
| LOC84989 | 22.61 | 0.13 | 0.23 | 1.47 |
| CTGF | 328.66 | 0.09 | 0.34 | 0.01 |
| ECM1 | 3.59 | 0.29 | 0.89 | 10.80 |
| CDKN2A | 3.79 | 0.06 | 0.31 | 3.00 |
| PENK | 42.46 | 0.03 | 0.05 | 0.82 |
| GAS2L3 | 3.30 | 0.77 | 0.20 | 4.08 |
| SERINC2 | 6.90 | 0.84 | 0.29 | 9.37 |
| GPM6B | 11.14 | 0.27 | 0.78 | 0.21 |
| PHLDA3 | 9.36 | 0.07 | 0.83 | 6.48 |

| Gene | Average mAML | Average mBALL | Average TCGA | Median TCGA | BM-WBC |
|---|---|---|---|---|---|
| CD70 | 96.56 | 12.01 | 2.85 | 0.38 | 0.60 |
| LAMP5 | 50.82 | 50.77 | 16.76 | 0.21 | 1.29 |
| THBS4 | 17.26 | 3.30 | 1.40 | 0.71 | 0.07 |
| LOC84989 | 12.40 | 6.73 | NA | NA | 0.00 |
| CTGF | 11.44 | 185.26 | 2.16 | 0.47 | 0.29 |
| ECM1 | 7.70 | 5.32 | 5.83 | 3.20 | 0.16 |
| CDKN2A | 7.05 | 4.30 | 3.00 | 1.60 | 0.28 |
| PENK | 5.89 | 89.83 | 0.35 | 0.00 | 0.30 |
| GAS2L3 | 4.95 | 4.38 | 1.52 | 1.23 | 0.31 |
| SERINC2 | 3.89 | 36.22 | 3.81 | 1.15 | 0.54 |
| GPM6B | 3.34 | 5.78 | 3.53 | 2.13 | 0.61 |
| PHLDA3 | 5.82 | 1.26 | 3.42 | 2.18 | 0.31 |

Average normalized gene expression values (Reads Per Kilobase pair of gene model per Million reads sequenced; RPKM) for 12 candidate genes are shown with RNA-seq data from: healthy donor monocytes (n = 2), CD34+ cells (n = 5), CD34+ cells after MA9 transduction (MA9, n = 3), model B-ALL (mBALL, n = 7) and AML (mAML, n = 9), pediatric MA9 AML patients (pAML, median shown, n = 3), adult AML from TCGA (average and median RPKM shown, n = 184) and in public RNA-seq data (Bodymap2 project) from purified white blood cells (BM-WBC). Candidate genes in this table were specifically selected to have clear expression (RPKM >3) in any MLL-AF9 leukemia (model AML/B-ALL, pediatric AML) sample but no expression (RPKM <1) in normal monocytes or CD34+ cells.

TABLE 3

Genbank/RefSeq and Uniprot accession numbers corresponding to the genes/proteins described herein

| Gene | Genbank/RefSeq nucleotide | Genbank/RefSeq protein | Uniprot |
|---|---|---|---|
| SYT17 | NM_016524.2. | NP_057608.2. | Q9BSW7 |
| DES | NM_003676.3. | NP_003667.1. | O15121 |
| IL31RA | NM_001242636.1. | NP_001229565.1. | Q8NI17 |
| | NM_001242637.1. | NP_001229566.1. | |
| | NM_001242638.1. | NP_001229567.1. | |
| | NM_001242639.1. | NP_001229568.1. | |
| | NM_139017.5. | NP_620586.3. | |
| CABP4 | NM_145200.3. | NP_660201.1. | P57796 |
| LPL | NM_000237.2. | NP_000228.1. | P06858 |
| CCL23 | NM_005064.4. | NP_005055.2. | P55773 |
| | NM_145898.2. | NP_665905.1. | |
| TRPM4 | NM_001195227.1. | NP_001182156.1. | Q8TD43 |
| | NM_017636.3. | NP_060106.2. | |
| MT1G | NM_005950.1. | NP_005941.1. | P13640 |
| RET | NM_020630.4. | NP_065681.1. | P07949 |
| | NM_020975.4. | NP_066124.1 | |
| C17orf55 | BC108932 | AAI08933.1. | Q8N8I6 |
| FAM70A | NM_001104544.1. | NP_001098014.1. | Q5JRV8 |
| | NM_001104545.1. | NP_001098015.1. | |
| | NM_017938.3. | NP_060408.3. | |
| RUFY4 | NM_198483.3. | NP_940885.2. | Q6ZNE9 |
| NRG4 | NM_138573.3. | NP_612640.1. | Q8WWG1 |
| KIF26B | NM_018012.3. | NP_060482.2. | Q2KJY2 |
| NAV3 | NM_001024383.1. | NP_001019554.1. | Q8IVL0 |
| | NM_014903.5. | NP_055718.4. | |
| ITGA7 | NM_001144996.1. | NP_001138468.1. | Q13683 |
| | NM_001144997.1. | NP_001138469.1 | |
| | NM_002206.2. | NP_002197.2. | |
| NXF3 | NM_022052.1. | NP_071335.1. | Q9H4D5 |
| PDZD7 | NM_01195263.1. | NP_001182192.1. | Q9H5P4 |
| | NM_024895.4. | NP_079171.1. | |
| CLSTN2 | NM_022131.2. | NP_071414.2. | Q9H4D0 |
| PHACTR3 | NM_001199505.1. | NP_001186434.1. | Q96KR7 |
| | NM_001199506.1. | NP_001186435.1. | |
| | NM_001281507.1. | NP_001268436.1. | |
| | NM_080672.4. | NP_542403.1. | |
| | NM_183244.1. | NP_899067.1. | |
| | NM_183246.1. | NP_899069.1. | |
| SCUBE1 | NM_173050.3. | NP_766638.2. | Q8IWY4 |
| SLC22A20 | NM_001004326.4. | NP_001004326.4. | A6NK97 |
| GIPR | NM_000164.2. | NP_000155.1. | P48546 |
| DYSFIP1 | NM_001007533.3. | NP_001007534.1. | Q86WC6 |
| DEFB1 | NM_005218.3. | NP_005209.1. | P60022 |
| METTL7B | NM_152637.2. | NP_689850.2. | Q6UX53 |
| BCL2L10 | NM_020396.2. | NP_065129.1. | Q9HD36 |
| LOC100289656 | NR_036475.2 | | |
| KCNN2 | NM_001278204.1. | NP_001265133.1. | Q9H2S1 |
| | NM_021614.3. | NP_067627.2. | |
| | NM_170775.2. | NP_740721.1. | |
| AGT | NM_000030.2. | NP_000021.1. | P21549 |
| LOC728606/PCAT18 | NR_024259.1 | | |
| SAGE1 | NM_018666.2. | NP_061136.2. | Q9NXZ1 |
| ARTN | NM_001136215.1. | NP_001129687.1. | Q5T4W7 |
| | NM_057090.2. | NP_476431.2. | |
| | NM_057091.2. | NP_476432.2. | |
| TGM5 | NM_178520.3. | NP_848615.1. | Q8N8V8 |
| PITX1 | NM_002653.4. | NP_002644.4. | P78337 |
| TMEM105 | NM_178520.3. | NP_848615.1. | Q8N8V8 |
| CD276 | NM_001024736.1. | NP_001019907.1. | Q5ZPR3 |
| | NM_025240.2. | NP_079516.1. | |
| CCDC144NL | NM_001004306.1. | NP_001004306.1. | Q6NUI1 |
| HOXA11 | NM_005523.5. | NP_005514.1. | P31270 |
| CD70 | NM_001252.4. | NP_001243.1. | P32970 |
| LAMP5 | NM_001199897.1. | NP_001186826.1. | Q9UJQ1 |
| | NM_012261.3. | NP_036393.1. | |
| THBS4 | NM_003248.4. | NP_003239.2. | P35443 |
| LOC84989 | BC007866.2 | | |
| CTGF | NM_001901.2. | NP_001892.1. | Q5M8T4 |
| ECM1 | NM_001202858.1.. | NP_001189787.1. | Q16610 |
| | NM_004425.3. | NP_004416.2 | |
| | NM_022664.2. | NP_073155.2. | |
| CDKN2A | NM_000077.4. | NP_000068.1. | P42771 |
| | NM_001195132.1. | NP_001182061.1. | |
| | NM_058197.4. | NP_478104.2. | |
| PENK | NM_001135690.1. | NP_001129162.1. | P01210 |
| | NM_006211.3. | NP_006202.1. | |
| GAS2L3 | NM_174942.1. | NP_777602.1. | Q86XJ1 |
| SERINC2 | NM_001199037.1. | NP_001185966.1. | Q96SA4 |
| | NM_001199038.1. | NP_001185967.1. | |
| | NM_001199039.1. | NP_001185968.1. | |
| | NM_018565.3. | NP_061035.2. | |
| | NM_178865.4. | NP_849196.2. | |

TABLE 3-continued

Genbank/RefSeq and Uniprot accession numbers corresponding to the genes/proteins described herein

| Gene | Genbank/RefSeq nucleotide | Genbank/RefSeq protein | Uniprot |
|---|---|---|---|
| GPM6B | NM_001001994.1. | NP_001001994.1. | Q13491 |
|  | NM_001001995.1. | NP_001001995.1. |  |
|  | NM_001001996.1. | NP_001001996.1. |  |
|  | NM_005278.3. | NP_005269.1. |  |
| PHLDA3 | NM_012396.3. | NP_036528.1. | Q9Y5J5 |

As used herein, the term "diagnosis" as used herein encompasses identification, confirmation, characterization and/or evaluation of the likelihood of a disease (leukemia, AML).

The present invention also provides a method for assessing minimal residual disease (MRD) in a patient suffering from AML, said method comprising (i) measuring the expression of one or more of the genes listed in Table 1 or Table 2 in a sample from the subject; (ii) comparing said expression to a control expression; and (iii) assessing MRD based on said comparing.

The present invention also provides a method for assessing minimal residual disease (MRD) in a patient suffering from MLL-AF9 AML, said method comprising (i) measuring the expression of one or more of the genes listed in Table 1 in a sample from the subject; (ii) comparing said expression to a control expression; and (iii) assessing MRD based on said comparing.

The present invention also provides a method for assessing minimal residual disease (MRD) in a patient suffering from MLL-AF9 leukemia, said method comprising (i) measuring the expression of one or more of the genes listed in Table 2 in a sample from the subject; (ii) comparing said expression to a control expression; and (iii) assessing MRD based on said comparing.

The determination of the expression and/or activity of the one or more genes or encoded gene products (e.g., mRNA, protein) may be performed using any known methods to detect nucleic acids or proteins. In embodiments, the expression or activity is compared to a control or reference level (e.g., the level obtained a sample from a healthy subject) to assess whether the subject suffers from leukemia, AML, MLL-AF9 leukemia or AML. As used herein, the term "measuring the expression of one or more of the genes" includes determining the level of one or more genes of interest by using any direct or indirect quantitative assay known to one of skill in the art. In certain instances, quantitative assays that determine, for example, the relative or absolute amount of RNA, mRNA, protein or activity are suitable for determining the level of one or more genes of interest. One skilled in the art will appreciate that any assay useful for determining the level of a gene is also useful for determining the presence or absence of the marker.

The levels of nucleic acid corresponding to the above-mentioned genes can then be evaluated according to the methods disclosed herein, e.g., with or without the use of nucleic acid amplification methods. In some embodiments, nucleic acid amplification methods can be used to detect the level of expression of the one or more genes. For example, the oligonucleotide primers and probes may be used in amplification and detection methods that use nucleic acid substrates isolated by any of a variety of well-known and established methodologies (e.g., Sambrook et al., Molecular Cloning, A laboratory Manual, pp. 7.37-7.57 (2nd ed., 1989); Lin et al., in Diagnostic Molecular Microbiology, Principles and Applications, pp. 605-16 (Persing et al., eds. (1993); Ausubel et al., Current Protocols in Molecular Biology (2001 and later updates thereto)). Methods for amplifying nucleic acids include, but are not limited to, for example the polymerase chain reaction (PCR) and reverse transcription PCR (RT-PCR) (see e.g., U.S. Pat. Nos. 4,683, 195; 4,683,202; 4,800,159; 4,965,188), ligase chain reaction (LCR) (see, e.g., Weiss, Science 254: 1292-93 (1991)), strand displacement amplification (SDA) (see e.g., Walker et al, Proc. Natl. Acad. Sci. USA 89:392-396 (1992); U.S. Pat. Nos. 5,270,184 and 5,455,166), Thermophilic SDA (tSDA) (see e.g., European Pat. No. 0 684 315) and methods described in U.S. Pat. No. 5,130,238; Lizardi et al., Bio-Technol. 6:1197-1202 (1988); Kwoh et al., Proc. Natl. Acad. Sci. USA 86:1173-77 (1989); Guatelli et al., Proc. Natl. Acad. Sci. USA 87:1874-78 (1990); U.S. Pat. Nos. 5,480, 784; 5,399,491; U.S. Publication No. 2006/46265, Serial Analysis of Gene Expression (SAGE), RNA sequencing (RNA-seq), microarray analysis, Luminex® MultiAnalyte Profiling (xMAP) technology and the like. The methods include the use of Transcription Mediated Amplification (TMA), which employs an RNA polymerase to produce multiple RNA transcripts of a target region (see, e.g., U.S. Pat. Nos. 5,480,784; 5,399,491 and US Publication No. 2006/46265).

The nucleic acid or amplification product may be detected or quantified by hybridizing a labeled probe to a portion of the nucleic acid or amplified product, and measuring the amount of probe/nucleic acid complexes using any suitable assay. In an embodiment, the labeled probe comprises a detectable group that may be, for example, a fluorescent moiety, chemiluminescent moiety, radioisotope, biotin, avidin, enzyme, enzyme substrate, or other reactive group. Other well-known detection techniques include, for example, gel filtration, gel electrophoresis and visualization of the amplicons, and High Performance Liquid Chromatography (HPLC). In certain embodiments, for example using real-time TMA or real-time PCR, the level of amplified product is detected as the product accumulates.

In an embodiment, the method comprises at least one of the following: obtaining or isolating mRNA from a sample from a subject, generating cDNA from the obtained mRNA, amplifying (specifically or non-specifically) the cDNA(s) corresponding to the one or more of the genes; and measuring the level of the cDNA(s), for example using a labelled oligonucleotide.

In another embodiment, the method comprises directly detecting mRNA levels (e.g., without generating/amplifying cDNA), for example using Northern blot, RNA Protection assay, DNA microarray (RPA) or any other method for direct mRNA quantification. In an embodiment, the method comprises labeling the mRNA, for example using a fluorescent moiety, a chemiluminescent moiety, a radioisotope or any other suitable labeling moiety.

In another embodiment, the expression and/or activity of the one or more genes or encoded gene products is measured at the protein/polypeptide level. Methods to measure the amount/level of proteins are well known in the art. Protein levels may be detected directly using a ligand binding specifically to the protein, such as an antibody or a fragment thereof. In embodiments, such a binding molecule or reagent (e.g., antibody) is labeled/conjugated, e.g., radio-labeled, chromophore-labeled, fluorophore-labeled, or enzyme-labeled to facilitate detection and quantification of the complex (direct detection). Alternatively, protein levels may be detected indirectly, using a binding molecule or reagent, followed by the detection of the [protein/binding molecule or reagent] complex using a second ligand (or second binding molecule) specifically recognizing the binding molecule or reagent (indirect detection). Such a second ligand may be radio-labeled, chromophore-labeled, fluorophore-labeled, or enzyme-labeled to facilitate detection and quantification of the complex. Enzymes used for labeling antibodies for immunoassays are known in the art, and the most widely used are horseradish peroxidase (HRP) and alkaline phosphatase (AP). Examples of binding molecules or reagents include antibodies (monoclonal or polyclonal), natural or synthetic ligands, and the like.

Examples of methods to measure the amount/level of protein in a sample include, but are not limited to: Western blot, immunoblot, immunoassays such as enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL), immunoprecipitation, surface plasmon resonance (SPR), chemiluminescence, fluorescent polarization, phosphorescence, immunohistochemical (IHC) analysis, matrix-assisted laser desorption/ionization time-of-flight (MALDI-TOF) mass spectrometry, microcytometry, microarray, antibody array, microscopy (e.g., electron microscopy), flow cytometry, proteomic-based assays, and assays based on a property of the protein including but not limited to ligand binding or interaction with other protein partners, enzymatic activity, fluorescence. For example, if the protein of interest is a kinase known to phosphorylate of given target, the level or activity of the protein of interest may be determined by the measuring the level of phosphorylation of the target in the presence of the test compound. If the protein of interest is a transcription factor known to induce the expression of given target gene, the level or activity of the protein of interest may be determined by the measuring the level of expression of the target gene.

The term "sample" includes any biological specimen obtained from an individual. Suitable samples for use in the present invention include, without limitation, whole blood, plasma, serum, saliva, urine, stool, sputum, tears, any other bodily fluid, tissue samples (e.g., biopsy), cellular extracts thereof (e.g., blood cell extract), cell samples (blood cells, bone marrow cells, etc.). One skilled in the art will appreciate that samples can be processed, e.g., dilution, purification, extraction of cellular components such as nucleic acids, etc., prior to the analysis of marker levels.

In an embodiment, the sample is a cell sample, in a further embodiment a cell sample comprising blood cells and/or bone marrow cells.

In an embodiment, the control level is a level measured in a non-cancerous (non-AML) cell sample, and (i) a higher level of expression in the sample from said subject is indicative that said subject has AML; or (ii) a similar or lower level of expression sample from said subject is indicative that said subject does not have AML.

In an embodiment, the control level is a level measured in a cancerous (AML) cell sample, and (i) a similar or higher level of expression in the sample from said subject is indicative that said subject has AML; or (ii) a lower level of expression in the sample from said subject is indicative that said subject does not have AML.

Table 4 below depicts the proteins among those identified herein that are known/predicted to be secreted. Accordingly, the levels of these proteins could be measured in any biological fluid sample containing the secreted proteins, such as a blood-derived sample (e.g., serum, plasma, whole blood or any sample containing the secreted proteins) to determine whether a subject suffers from AML. As such, these proteins could be used in a similar fashion as the current prostate specific antigen (PSA) test, where elevated blood concentrations of PSA are indicative of (or strongly suggest) the presence of prostate cancer in the subject.

TABLE 4

Proteins that are known/predicted to be secreted

| Protein | Uniprot accession No. |
| --- | --- |
| SCUBE1 | Q8IWY4 |
| LPL | P06858 |
| CCL23 | P55773 |
| DEFB1 | P60022 |
| AGT | P21549 |
| ARTN | Q5T4W7 |
| THBS4 | P35443 |
| CTGF | Q5M8T4 |
| ECM1 | Q16610 |
| PENK | P01210 |

Accordingly, in another aspect, the present invention provides a method for determining whether a subject suffers from acute myeloid leukemia (AML), said method comprising (i) measuring the level of one or more of the proteins listed in Table 4 in a biological fluid sample from the subject; (ii) comparing said level to a control level; and (iii) determining whether the subject suffers from AML based on said comparing. In an embodiment, the biological fluid sample is a blood-derived sample (e.g., serum, plasma, or whole blood. In an embodiment, the method comprising one or more of the following: obtaining a biological fluid sample from the subject, contacting the biological fluid sample with a ligand specifically binding to the one or more of the proteins listed in Table 4, measuring the level of protein/ligand complexes, and/or comparing the level of protein/ligand complexes to a control level. The ligand may a natural or synthetic ligand of the protein, as defined above. In an embodiment, the ligand is labelled with a detectable moiety, for example a fluorescent moiety. In an embodiment, the ligand is an antibody specifically binding to the one or more of the proteins listed in Table 4.

"Control expression/level" or "reference expression/level" or "standard expression/level" are used interchangeably herein and broadly refers to a separate baseline level measured in a comparable "control" sample, which is generally from a subject not suffering from the disease (AML) or not at risk of suffering from the disease. Alternatively, in another embodiment, the comparable "control" sample is from a subject not suffering the disease (AML) or at risk of suffering from the disease. The corresponding control expression/level may be a level corresponding to an average or median expression/level calculated based of the levels measured in several reference or control subjects (e.g., a pre-determined or established standard level). The control level may be a pre-determined "cut-off" value recognized in the art or established based on levels measured in samples from one or a group of control subjects. The corresponding reference/control level may be adjusted or normalized for age, gender, race, or other parameters. The "control level" can thus be a single number/value, equally applicable to every patient individually, or the control level can vary, according to specific subpopulations of patients. Thus, for example, older men might have a different control level than younger men, and women might have a different control level than men. The predetermined standard level can be arranged, for example, where a tested population is divided equally (or unequally) into groups, such as a low-risk group, a medium-risk group and a high-risk group or into quadrants or quintiles, the lowest quadrant or quintile being individuals with the lowest risk (i.e., lowest level of expression of the one or more genes) and the highest quadrant or quintile being individuals with the highest risk (i.e., highest level of expression of the one or more genes).

It will also be understood that the control levels according to the invention may be, in addition to predetermined levels or standards, levels measured in other samples (e.g. from healthy/normal subjects, or cancer patients) tested in parallel with the experimental sample.

In embodiments, the cut-off value may be determined using a Receiver Operator Curve, according to the method of Sackett et al., *Clinical Epidemiology: A Basic Science for Clinical Medicine*, pp. 106-7 (1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher or lower than the cut-off value determined by this method may be considered positive. Alternatively, the cut-off value may be shifted to the left along the plot, to minimize the false positive rate, or to the right, to minimize the false negative rate. In general, a sample generating a signal that is higher or lower than the cut-off value determined by this method is considered positive for a cancer (AML).

In an embodiment, the control expression/level is an expression/level measured in a normal stem cell and/or hematopoietic progenitor cell sample.

"Higher expression" or "higher level of expression" as used herein refers to (i) higher expression of the one or more genes listed in Table 1 or 2 (protein and/or mRNA) in one or more given cells present in the sample (relative to the control) and/or (ii) higher amount of cells expressing the one or more genes listed in Table 1 or 2 in the sample (relative to the control). "Lower expression" or "lower level of expression" as used herein refers to (i) lower expression of the one or more genes listed in Table 1 or 2 (protein and/or mRNA) in one or more given cells present in the sample (relative to the control) and/or (ii) lower amount of cells expressing the one or more genes listed in Table 1 or 2 in the sample (relative to the control). In an embodiment, higher or lower refers to a level of expression that is at least one standard deviation above or below the control level (e.g., the predetermined cut-off value), and a "similar expression" or "similar level of expression" refers to a level of expression that is less than one standard deviation above or below the control level (e.g., the predetermined cut-off value). In embodiments, higher or lower refers to a level of expression that is at least 1.5, 2, 2.5 or 3 standard deviations above or below the control level (e.g., the predetermined cut-off value), and a "similar expression" or "similar level of expression" refers to a level of expression that is less than 1.5, 2, 2.5 or 3 standard deviation above or below the control level (e.g., the predetermined cut-off value). In another embodiment, "higher expression" refers to an expression that is at least 20, 25, 30, 35, 40, 45, or 50% higher in the test sample relative to the control level. In an embodiment, "lower expression" refers to an expression that is at least 20, 25, 30, 35, 40, 45, or 50% lower in the test sample relative to the control level. In an embodiment, "similar expression" refers to an expression that varies by less than 20, 15, or 10% between the test sample and the control level.

In an embodiment, the markers identified herein may be useful to follow-up the condition of a patient over time. The method comprises (a) determining a first level of expression of the one or more genes listed in Table 1 or 2 (or the proteins listed in Table 4) in a sample; wherein a decrease in said first level relative to a corresponding level determined in a corresponding biological sample obtained from said subject at an earlier time (e.g., before treatment or during treatment but at an earlier time point) is indicative that said patient condition has improved (e.g., that the cancer has regressed, that the treatment is effective), and wherein an increase in said first level (or a similar level) relative to a corresponding level determined in a corresponding biological sample obtained from said subject at an earlier time (e.g., before treatment or during treatment but at an earlier time point) is indicative that said patient condition has deteriorated (e.g., that the cancer has progressed or has not regressed, that the treatment is not effective). If it is determined that the treatment is not effective in the subject, a different and/or more aggressive anti-leukemia therapy may be used. Also, the levels of the one or more genes listed in Table 1 or 2 (or the proteins listed in Table 4) at the later time point may indicate whether further anti-leukemia therapy are required.

In an embodiment, the method comprising measuring the expression of a plurality of the genes listed in Table 1 or 2 (or the proteins listed in Table 4), for example at least 2, 3, 4, 5, 6, 7, 8, 9 or 10 of the genes/proteins. In another embodiment, the method comprising measuring the expression of all the genes listed in Table 1 or 2 (or the proteins listed in Table 4).

In embodiments, the gene expression values or levels are subjected to one or more transformation analyses, such as statistical analysis/transformation. As used herein, "transformation analyses" can be any suitable mathematical operation, including but not limited to generalized models (e.g., logistic or logit regression, ROC regression, generalized additive models), multivariate analysis (e.g., discriminant analysis, principal components analysis, factor analysis). For example, the one or more transformation analyses may comprise logistic regression analysis, and in a further embodiment the logistic regression analysis comprises (i) adjusting the value of one or more of the gene expression values or levels by an appropriate weighting coefficient (e.g., regression coefficient) to produce a weighted score for each gene expression values or levels, and (ii) combining the weighted score for each gene expression values or levels to generate the probability score (e.g. the probability that the subject suffers from a disease (e.g., leukemia, AML, MLL-AF9 leukemia or AML). In various embodiments, the levels of one, two, three, four, five, or more gene expression values or levels may be adjusted by an appropriate weighting coefficient. The transformation analysis may be performed using a suitable software, such as the Statistical Analysis Software (SAS).

As will be understood by those of skill in the art, weighting coefficients can be determined by a variety of techniques and can vary widely. In one example of determining appropriate weighting coefficients, multiple logistic regression (MLR) is performed using the gene expression values or levels measured within two groups of patients or samples, for example, one with a disease (e.g., leukemia, AML, MLL-AF9 leukemia or AML) and one without the disease. There are several methods for variable (gene expression values or levels) selection that can be used with MLR, whereby the gene expression values or levels not selected are eliminated from the model and the weighting coefficients for each predictive ERG parameter remaining in the model are determined. These weighting coefficients can then be, for example, multiplied by the gene expression values or levels measured in the subject/sample and then, for example, summed to calculate a probability score (e.g., the probability that the subject suffers from a disease (e.g., leukemia, AML, MLL-AF9 leukemia or AML). Other parameters/variables may be incorporated as covariate in the model, such as age, gender and/or ethnicity, etc.

In an embodiment, the above-mentioned method is an aid for the diagnosis of leukemia, AML, MLL-AF9 leukemia or AML. Accordingly, the above-mentioned methods may be performed in combination with other methods or markers for diagnosing leukemia, AML, MLL-AF9 leukemia or AML, for example, family history, medical assessment, symptoms, presence of biological and/or genetic markers associated with leukemia, AML, MLL-AF9 leukemia or AML, etc. In another embodiment, the above-mentioned methods are performed on subjects suspected of suffering from leukemia, AML, MLL-AF9 leukemia or AML, and are used to confirm the diagnosis.

The present invention also provides an assay mixture comprising means/reagents for determining the amount/level of one or more genes listed in Table 1 or 2 (or the proteins listed in Table 4), for example one or more ligands that specifically bind to proteins such as a specific antibody or oligonucleotides (probes, primers) that hybridizes to a nucleic acid (mRNA, cDNA) corresponding to the one or more genes. The assay mixture further comprises a sample from a subject suspected of suffering from AML. The assay mixture may further comprise a container containing the sample and the means/reagents for determining the amount/level of one or more genes listed in Table 1 or 2 (or the proteins listed in Table 4), reagents to perform the methods defined above including buffers, enzymes (e.g., enzymes for amplification), etc.

The present invention also provides a kit comprising means/reagents for determining the amount/level of one or more genes listed in Table 1 or 2 (or the proteins listed in Table 4), for example one or more ligands that specifically bind to proteins such as a specific antibody or oligonucleotides (probes, primers) that hybridizes to a nucleic acid (mRNA, cDNA) corresponding to the one or more genes. Such kit may further comprise, for example, instructions setting forth the above-mentioned methods (i.e., instructions for diagnosing leukemia, AML, for following-up the course of treatment or condition of a subject), control samples (e.g., samples to which the test sample may be compared to establish the diagnosis/prediction), containers, reagents useful for performing the methods (e.g., buffers, enzymes, containers, immunodetection reagents, etc). The kit may further include where necessary agents for reducing background interference in a test, agents for increasing signal, software and algorithms for combining and interpolating values to produce a prediction of clinical outcome of interest, apparatus for conducting a test, calibration curves and charts, standardization curves and charts, and the like.

In an embodiment, the above-mentioned method further comprises selecting and/or administering a course of therapy or prophylaxis to said subject in accordance with the diagnostic result. If it is determined that the subject has AML, the method further comprises subjecting the subject to a suitable anticancer therapy (e.g., bone marrow transplantation, chemotherapy, etc.). Thus, in another aspect, the present invention provides a method for treating acute myeloid leukemia (AML) in a subject, said method comprising (i) identifying a subject suffering from AML using the methods defined above and (ii) subjecting the subject suffering from AML to a suitable anti-cancer/anti-leukemia therapy (e.g., bone marrow transplantation, chemotherapy, immunotherapy, antibody-based therapy, etc.). In an embodiment, the method comprises detecting the presence of one or more of the cell surface proteins listed in Table 4 below and, if the one or more the cell surface proteins is detected in the sample from the subject, administering an effective amount of an antibody directed against said one or more cell surface proteins.

Treatment of AML

Current conventional cancer therapies typically entail treatment with repeated doses of chemotherapeutic agents (such as cyclophosphamide, etoposide and doxorubicin), these treatments are non-specific, and therefore target healthy cells as well. The destruction of normal cells can lead to severe, sometimes fatal, side-effects in many cases, in addition to long-term damage to normal cellular tissues. The development of treatments that can specifically target cancer cells with no or minimal effects on normal cells is therefore a priority within the field of cancer research.

One mechanism to achieve this is through the development of specific antibodies against cell surface proteins that are only present on tumor cells. Such antibodies can be injected into patients and will then bind the cognate protein epitopes on the tumor cells. Once the antibody binds the tumor protein, the non-variable base of the antibody (also called the Fc region) can then be recognized by cells of the human immune system. Specific immune cells (such as natural killer cells or NK cells) have receptors (i.e. CD16) which recognize the Fc portion of antibodies. The recognition of target cells with bound antibodies leads to the activation of NK cells (and/or other cytotoxic cells such as macrophages, monocytes and/or eosinophils) which then destroy the target cell through processes called antibody-Dependent Cell-Mediated Cytotoxicity (ADCC) and/or antibody-dependent cellular phagocytosis (ADCP). The binding of antibodies to the cognate protein epitopes on the tumor cells may also lead to killing of the tumor cells through a mechanism called complement-dependent cytotoxicity (CDC). In CDC, the C1q complex of the complement system binds the antibody and this binding triggers the complement cascade which leads to the formation of the membrane attack complex (MAC) (C5b to C9) at the surface of the target cell, as a result of the classical pathway complement activation. Antibodies may also interfere with or modulate the activity of the cell surface proteins in tumor cells, e.g., by blocking the interaction with a ligand, thereby modulating the signaling within the tumor cells (which may in turn affect tumor cell proliferation, survival and/or migration. The antibody may alternatively or further be conjugated to an anti-tumor agent (chemotherapeutic agent, toxin) so as to deliver the anti-tumor agent to the tumor cells that expressed the cell surface markers, i.e. using the antibody or antigen-binding fragment thereof as a targeting agent for tumor cells.

It is therefore possible, with knowledge of proteins that are specifically expressed on the surface of tumor cells, where they are accessible to the antibodies, to develop targeted anti-cancer therapies which function through antibody-based cell cytotoxicity (ADCC, ADCP and CDC).

This approach has been used successfully to target ERBB2 receptor in certain breast cancers (with Trastuzumab; *Nat Med.* 2000 April; 6(4):443-6), the EGF receptor in metastatic colorectal cancer and head and neck cancer (Cetuximab; Lancet Oncol. 2010 January; 11(1):21-8. doi: 10.1016/S1470-2045(09)70311-0. Epub 2009 Nov. 10.), the CD20 protein in lymphomas and leukemias (e.g., with Rituximab; Blood. 1997 Sep. 15; 90(6):2188-95; Ofatumumab and others; *J Hematol Oncol.* 2012 Oct. 11; 5:64), the CD38 protein in multiple myeloma (with Daratumumab; *J Immunol.* 2011 Feb. 1; 186(3):1840-8). It is also possible to improve the effectiveness of the ADCC response through additional protein modifications to the antibody (*Eur J Cancer.* 2013 October; 49(15):3344-52. doi: 10.1016/j.ejca.2013.06.009. Epub 2013 Jul. 18).

Table 5 below depicts the proteins among those identified herein that are known/predicted to be expressed at the cell surface of acute myeloid leukemia cells but not in normal blood and are generally absent or expressed at low levels in a wide variety of other normal tissues. Accordingly, these proteins constitute good targets for antibody-based anti-leukemia therapy.

TABLE 5

Proteins that are known/predicted to be expressed at the cell surface

| Protein | Uniprot accession No. | Residues defining the extracellular domain(s) according to Uniprot | Existing antibody (flow cytometry) |
| --- | --- | --- | --- |
| SYT17 | Q9BSW7 | | |
| FAM70A/ TMEM255A | Q5JRV8 | | |
| NRG4 | Q8WWG1 | 1-62 | |
| CLSTN2 | Q9H4D0 | 21-831 | |
| SLC22A20 | A6NK97 | 45-137; 188-194; 247-250; 361-373; 419-429; 507-555 | |
| GIPR | P48546 | 22-138; 190-217; 279-293; 363-377 | Thermo Scientific ® (Pierce), Cat. No. PA5-14408 |
| KCNN2 | Q9H2S1 | | |
| TMEM105 | Q8N8V8 | | |
| CD276 | Q5ZPR3 | 29-466 | |
| IL31RA | Q8NI17 | 20-519 | R&D Systems ®, Cat. No. AF2769 |
| TRPM4 | Q8TD43 | 705-776; 890-892; 951-965; 994-1019 | |
| RET | P07949 | 29-635 | Cell Signaling Technology ®, Cat. No. 3223S |
| ITGA7 | Q13683 | 34-1082 | Abcam ®, Cat. No. ab75224 |
| CD70 | P32970 | 39-193 | Abcam ®, Cat. No. ab77868 |
| LAMP5 | Q9UJQ1 | 30-235 | |
| SERINC2 | Q96SA4 | | |
| GPM6B | Q13491 | | |
| SCUBE1 | Q8IWY4 | | |

Accordingly, in another aspect, the present invention provides a method for treating acute myeloid leukemia (AML) in a subject, said method comprising administering to said subject an effective amount of an antibody that binds to a cell surface protein among the proteins encoded by the genes set forth in Tables 1 and 2, or an antigen-binding fragment thereof.

In an embodiment, the cell surface protein is a protein listed in Table 5 above. In an embodiment, the antibody binds to one or more epitopes located in the extracellular domain (ectodomain) of the protein.

The terms "antibody" and "antigen-binding fragment" are used in the broadest sense, and covers monoclonal antibodies (including full-length monoclonal antibodies), polyclonal antibodies, humanized antibodies, CDR-grafted antibodies, chimeric antibodies, multispecific antibodies, antibody fragments and antibody-like molecules so long as they exhibit the desired biological activity (e.g., binding to the target protein at the surface of tumor cells and induction of tumor cell killing). An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

Antibody fragments (i.e. antigen-binding fragments) comprise a portion of a full length antibody, generally an antigen binding or variable region thereof. Examples of antibody fragments and antibody-like molecules include Fab, Fab', F(ab')2, and Fv fragments, diabodies, bispecific antibodies (bsAbs), tandem scFvs, linear antibodies, single-chain antibody molecules, single domain antibodies (e.g., from camelids), shark NAR single domain antibodies, multispecific antibodies formed from antibody fragments, binding moieties comprising CDRs or antigen binding domains including, but not limited to, $V_H$ regions ($V_H$, $V_H$-$V_H$), anticalins, PepBodies, antibody-T-cell epitope fusions (Troybodies), Peptibodies, DARPins, adnectins (see, e.g., Shuptrine et al., *Semin Cancer Biol.* February 2012; 22(1): 3-13).

An antibody, an antibody conjugate, or an antibody fragment that "preferentially binds" or "specifically binds" (used interchangeably herein) to a target (e.g., a protein listed in Table 5) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity to the target protein than it does with other proteins. An antibody "specifically binds" or "preferentially binds" to a target protein if it binds with greater affinity, avidity, more readily, and/or with greater duration than it binds to other proteins. It is also understood that by reading this definition, for example, an antibody that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5$^{th}$ ed., 1991, National Institutes of Health, Bethesda Md.)); and (2) an approach based on crystallographic studies of antigen-antibody complexes (Al-lazikani et al., 1997, *J. Molec. Biol.* 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5$^{th}$ ed., Public Health Service, NIH, Washington D.C. The positions of the CDRs may also be identified as the structural loop structures originally described by Chothia and others. See, e.g., Chothia et al., *Nature* 342:877-883, 1989. Other approaches to CDR identification include the "AbM definition," which is a compromise between Kabat and Chothia and is derived using Oxford Molecular's AbM antibody modeling software (Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1 156-1 166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories).

Polyclonal antibodies are preferably raised in animals by multiple subcutaneous (s.c.), intravenous (i.v.) or intraperitoneal (i.p.) injections of the relevant antigen (e.g., a protein of Table 5, the extracellular domain thereof, or a fragment thereof) with or without an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals may be immunized against the antigen, immunogenic conjugates, or derivatives by combining the antigen or conjugate (e.g., 100 µg for rabbits or 5 µg for mice) with 3 volumes of Freund's complete adjuvant and injecting the solution intradermally at multiple sites. One month later the animals are boosted with the antigen or conjugate (e.g., with ⅕ to ¹⁄₁₀ of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293.

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Based on the sequences of the polypeptides encoded by the above-mentioned genes (which may be easily retrieved using the Uniprot accession Nos. in Tables 3 or 5), the skilled person would be able to generate antibodies, antibody fragments or antibody-like molecules) directed against these polypeptides (using the entire protein or a fragment thereof, such as the extracellular domain or a fragment thereof), which in turn may be used to bind to the target protein at the surface of tumor cells and induce tumor cell killing. Furthermore, antibodies directed against some of the protein listed in Table 5 are known in the art and commercially available.

As used herein, "humanized" antibody refers to forms of non-human (e.g. murine) antibodies that are chimeric immunoglobulins, immunoglobulin chains, or fragments thereof (such as Fv, Fab, Fab', F(ab')2 or other antigen binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in PCT publication No. WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., *Nature Biotechnology,* 14:309-314, 1996; Sheets et al., *Proc. Natl. Acad. Sci.* (*USA*) 95:6157-6162, 1998; Hoogenboom and Winter, *J. Mol. Biol.,* 227:381, 1991; Marks et al., J. Mol. Biol., 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boerner et al., *J. Immunol.,* 147(1):86-95, 1991; and U.S. Pat. No. 5,750,373.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007). In an alternative, a polynucleotide sequence encoding a chain of an antibody may be used for genetic manipulation to "humanize" the antibody or to improve the affinity, or other characteristics of the antibody. For example, it may be desirable to genetically manipulate the antibody sequence to obtain greater affinity to the target protein and/or greater efficacy in inducing tumour cell killing.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen binding site derived from a non-human immunoglobulin have been described, including chimeric antibodies having rodent or modified rodent V regions and their associated CDRs fused to human constant regions. See, for example, Winter et al. Nature 349:293-299, 1991, Lobuglio et al. Proc. Nat. Acad. Sci. USA 86:4220-4224, 1989, Shaw et al. J Immunol. 138:4534-4538, 1987, and Brown et al. Cancer Res. 47:3577-3583, 1987. Other references describe rodent CDRs grafted into a human supporting framework region (FR) prior to fusion with an appropriate human antibody constant region. See, for example, Riechmann et al. Nature 332:323-327, 1988, Verhoeyen et al. Science 239:1534-1536, 1988, and Jones et al. Nature 321: 522-525, 1986.

The general principles related to humanized antibodies discussed above are also applicable to customizing antibodies for use, for example, in dogs, cats, primate, equines and bovines. Further, one or more aspects of humanizing an antibody described herein may be combined, e.g., CDR grafting, framework mutation and CDR mutation.

In one variation, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743; and 6,265,150; and Winter et al., Annu. Rev. Immunol. 12:433-455, 1994. Alternatively, the phage display technology (McCafferty et al., Nature 348: 552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597, 1991, or Griffith et al., EMBO J. 12:725-734, 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783, 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., *Nucl. Acids Res.* 21: 2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., humanized, single chain, etc. are known in the art.

In an embodiment, the antibody or antigen-binding fragment comprises a Fc region or a functional variant thereof that is recognized by an Fc receptor present on an immune cell. As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from Pro230, to about the carboxyl-terminus thereof. The numbering of the residues in the Fc region is that of the EU index as in Kabat (Kabat et al., supra). The Fc region of an immunoglobulin generally comprises two constant regions, CH2 and CH3. A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; and/or phagocytosis. Such effector functions may be assessed using various assays known in the art for evaluating such antibody effector functions. A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Ann. Rev. Immunol., 9:457-92, 1991; Capel et al., Immunomethods, 4:25-34, 1994; and de Haas et al., J. Lab. Clin. Med., 126:330-41, 1995.

ADCC activity of a molecule of interest can be assessed using an in vitro ADCC assay, such as that described in U.S. Pat. Nos. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, PNAS (USA), 95:652-656.

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202: 163 (1996), may be performed.

The present invention also provides a conjugate (or immunoconjugate) of the antibody as described herein, or of the antigen binding fragment thereof, wherein the antibody or the antigen binding fragment is conjugated to an agent (e.g., a cytotoxic agent) for targeted immunotherapy (e.g., antibody-drug conjugates) either directly or indirectly via a linker, such as peptide linker. For example, a cytotoxic agent can be linked or conjugated to the antibody antibody or the antigen binding fragment thereof as described herein for targeted local delivery of the cytotoxic agent moiety to tumors (e.g., a tumour expressing the target protein).

Methods for conjugating cytotoxic agent or other therapeutic agents to antibodies have been described in various publications. For example, chemical modification can be made in the antibodies either through lysine side chain amines or through cysteine sulfhydryl groups activated by reducing interchain disulfide bonds for the conjugation reaction to occur. See, e.g., Tanaka et al., FEBS Letters 579:2092-2096, 2005, and Gentle et al., Bioconjugate Chem. 15:658-663, 2004. Reactive cysteine residues engineered at specific sites of antibodies for specific drug conjugation with defined stoichiometry have also been described. See, e.g., Junutula et al., Nature Biotechnology, 26:925-932, 2008. Conjugation using an acyl donor glutamine-containing tag or an endogenous glutamine made reactive (i.e., the ability to form a covalent bond as an acyl donor) by polypeptide engineering in the presence of transglutaminase and an amine (e.g., a cytotoxic agent comprising or attached to a reactive amine) is also described in International Patent Application Serial No. PCT/IB2011/054899 (WO2012/059882).

The agents that can be conjugated to the antibodies or the antigen binding fragments of the present invention include, but are not limited to, cytotoxic agents, immunomodulating agents, imaging agents, therapeutic proteins, biopolymers, or oligonucleotides.

In some embodiments, the agent is an imaging agent (e.g., a fluorescent moiety or a PET (Positron Emission Tomography) label, SPECT (Single-Photon Emission Computed Tomography) label), or MRI (Magnetic Resonance Imaging) label. Such antibodies may be used to detect tumour cells (MLL-AF9 leukemia cells) in vivo or in vitro using techniques known in the art, for example flow cytometry, immunochemistry, etc.

An "effective amount" refers to an amount effective, at dosages and for periods of time necessary, to achieve the desired therapeutic result. An effective amount refers to the amount of active compound or pharmaceutical agent (antibody or fragment thereof) that elicits the biological or medicinal response in a tissue, system, animal, individual or human that is being sought by a researcher, veterinarian, medical doctor or other clinician, which includes one or more of the following: (A) inhibiting the disease; for example, inhibiting a leukemia/AML in an individual that is experiencing or displaying the pathology or symptomatology of the disease, condition or disorder (i.e., arresting further development of the pathology and/or symptomatology, eliminating cancer cells,), and (B) ameliorating the disease; for example, ameliorating leukemia/AML in an individual that is experiencing or displaying the pathology or symptomatology of the disease, condition or disorder (i.e., reversing the pathology and/or symptomatology).

The amount of the antibody or antigen-binding fragment thereof which is effective in the treatment of leukemia/AML will depend on the nature and severity of the disease, the chosen therapeutic regimen, the target site of action, the patient's age, weight, special diets being followed by the patient, concurrent medications being used, the administration route and other factors that will be recognized by those skilled in the art. The dosage will be adapted by the clinician in accordance with conventional factors such as the extent of the disease and different parameters from the patient. Typically, 0.001 to 1000 mg/kg of body weight/day will be administered to the subject. In an embodiment, a daily dose range of about 0.01 mg/kg to about 500 mg/kg, in a further embodiment of about 0.1 mg/kg to about 200 mg/kg, in a further embodiment of about 1 mg/kg to about 100 mg/kg, in a further embodiment of about 10 mg/kg to about 50 mg/kg, may be used. The dose administered to a patient, in the context of the present invention should be sufficient to effect/induce a beneficial therapeutic response in the patient over time. The size of the dose also will be determined by the existence, nature, and extent of any adverse side-effects that accompany the administration. Effective doses may be extrapolated from dose response curves derived from in vitro or animal model test systems. For example, in order to obtain an effective mg/kg dose for humans based on data generated from rat studies, the effective mg/kg dosage in rat may be divided by six.

In an embodiment, the above-mentioned treatment comprises the use/administration of more than one (i.e. a combination of) active/therapeutic agent, including the above-mentioned antibody or antigen-binding fragment thereof. The combination of therapeutic agents and/or compositions of the present invention may be administered or co-administered (e.g., consecutively, simultaneously, at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the antibody or antigen-binding fragment thereof is used/administered in combination with one or more agent(s) or therapy currently used to prevent or treat the disorder in question, (e.g., chemotherapy, radiotherapy, bone marrow transplantation, hormone therapy, additional immunotherapy, etc.).

The above-mentioned antibody may be provided in a composition (e.g., a pharmaceutical composition) comprising a carrier, diluent and/or excipient (e.g., a pharmaceutically acceptable carrier, diluent and/or excipient). As used herein "pharmaceutically acceptable carrier" or "excipient" includes any and all solvents, buffers, dispersion media, coatings, antibacterial and antifungal agents, isotonic and absorption delaying agents, and the like that are physiologically compatible. The carrier can be suitable, for example, for intravenous, parenteral, subcutaneous, intramuscular, intracranial, intraorbital, ophthalmic, intraventricular, intracapsular, intraspinal, intrathecal, epidural, intracisternal, intraperitoneal, intranasal or pulmonary (e.g., aerosol) administration.

Pharmaceutically acceptable carriers include sterile aqueous solutions or dispersions and sterile powders for the extemporaneous preparation of sterile injectable solutions or dispersion. The use of such media and agents for pharmaceutically active substances is well known in the art (Rowe et al., Handbook of pharmaceutical excipients, 2003, 4$^{th}$ edition, Pharmaceutical Press, London UK). Except insofar as any conventional media or agent is incompatible with the active agent, use thereof in the pharmaceutical compositions of the invention is contemplated.

The above-mentioned antibody/antigen-binding fragment (or composition comprising same) may be administered, or adapted for administration, by any route of administration including oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. Therapeutic antibodies are typically administered through the intravenous, intramuscular or subcutaneous route.

In an embodiment, the AML involves translocation of the mixed-lineage leukemia (MLL) gene. In a further embodiment, the AML is MLL-AF9 positive AML.

MODE(S) FOR CARRYING OUT THE INVENTION

The present invention is illustrated in further details by the following non-limiting examples.

Example 1: Materials and Methods

Model Leukemias

Using previously validated methodology, CD34$^+$ enriched CB samples (~1×10$^6$ cells) from single donors (Stem Cell Technologies; STI, Vancouver or isolated in our laboratory) were transduced with a retrovirus containing GFP and the human MA9 fusion gene. Donor cells were split into two fractions: The first (1×10$^5$ cells) was used for RNA-seq and exome sequencing in order to identify the mutations present and measure gene expression levels prior to MA9 introduction. The second fraction (0.7×10$^6$ cells) was transduced with the fusion gene and expanded in myeloid promoting culture with 15% FSC+IL3+SCF for after 4 weeks of in vitro culture growth. After this time, cells (5×10$^6$/mouse) were injected into multiple NSG immunodeficient mice for each donor sample and separate samples (all of which have been lentivirally transduced) were maintained in culture (80-90 days total) before being collected for RNA sequencing. Mice typically developed leukemias after ~20-24 weeks and were sacrificed and the bone marrow was harvested. Cells collected were characterized by FACS with aliquots directly transferred to Trizol® (samples with >80% blasts in bone marrow; samples with <80% were FACS sorted to enrich for GFP positive (transduced) cells). After receiving the RNA collected from 0.5×10$^6$-1×10$^7$ cells, the material was used for RNA-seq using the standard Illumina® protocols at the Institut de Recherche en Immunologie et Cancérologie (IRIC) genomics facility. An outline of the procedure used is shown in FIG. 1.

Pediatric Leukemia Samples, Cell Lines and Other Cell Types

Pediatric AML samples collected under informed consent were obtained from the Banque de Cellules Leucémiques du Quebec/Quebec Leukemia Cell Bank (BCLQ) after ethics approval from University of Montreal for the sequencing project. Bone marrow cells in Trizol® were used for RNA extraction and additional clinical information for samples was collected from the BCLQ for these samples. RNA-seq was performed using the standard Illumina® RNA-seq protocols at the IRIC genomics facility. Various AML cell lines used for analysis were grown in vitro in supplemented media and 5×10$^6$ cells were briefly washed and placed into Trizol®. RNA was extracted according to the manufacturer's instructions and used as input for Illumina® RNA-seq, again according to standard manufacturer's protocols (see below). Fresh cord blood samples (<24 hr after isolation) collected under informed consent at Centre Hospitalier Universitaire (CHU) Ste-Justine by Dr. Sonia Cellot were used to isolate CD34$^+$ and monocyte cells from individual donors. These cell populations were placed into Trizol® and RNA was extracted and sequenced as described above.

RNA-Seq Sequencing

Paired-end barcoded Illumina™ sequencing libraries were generated using standard protocols tested at the IRIC genomics facility starting from 0.1-1 ug of total RNA or 100 ng of gDNA. rRNA was removed using a bead selection kit (Ambion™) or other selection reagents (Ribominus, Invitrogen) and exon capture was performed on gDNA using Illumina TruSeq™ exome enrichment kit (62 Mbp capture region). Libraries generated 100 bp reads from either end of single DNA molecules and were sequenced to generate ~1×10$^8$ reads per RNA sample. This sequencing depth provides a mean coverage of 50× (each nucleotide in a transcript is covered by 50 independent sequence reads) for transcribed genes and is sufficient to allow actively transcribed genes to be distinguished from transcriptional noise (generally transcripts with <1× coverage) and quantify splicing changes.

Data Analysis

Figure 3:
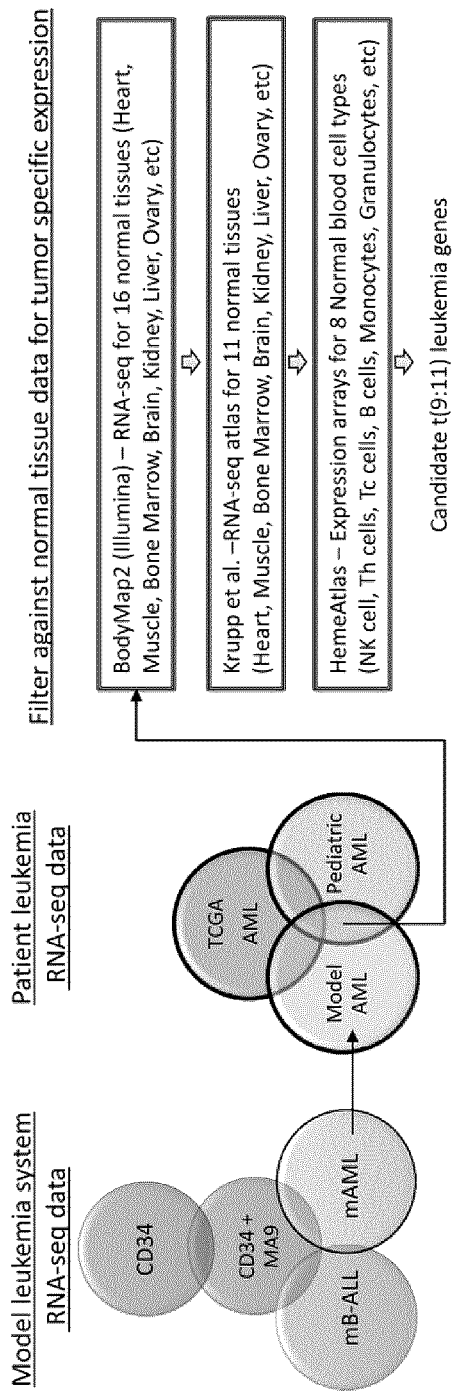
FIG. 3 shows the analysis methodology for identifying MA9-AML candidate genes. RNA-seq data from model leukemia system was used to identify genes that were expressed in all model AML samples (mAML) but were not expressed (RPKM<1) in model B-ALL (mB-ALL) or $CD34^+$ cord blood cells (CD34). These candidate genes were then compared to pediatric MA9 AML samples and adult AML data from TCGA (of which only 6/184 had MA9 translocations). Genes with consistent expression in model and pediatric AML samples (RPKM>5) but not TCGA AML were then filtered against various RNA-seq/microarray expression data for normal tissues/cells. Genes without expression (RPKM<1) in a majority of normal tissues and 6/8 blood cell types were taken as final candidate MA9-AML associated genes.
Figure 4A:
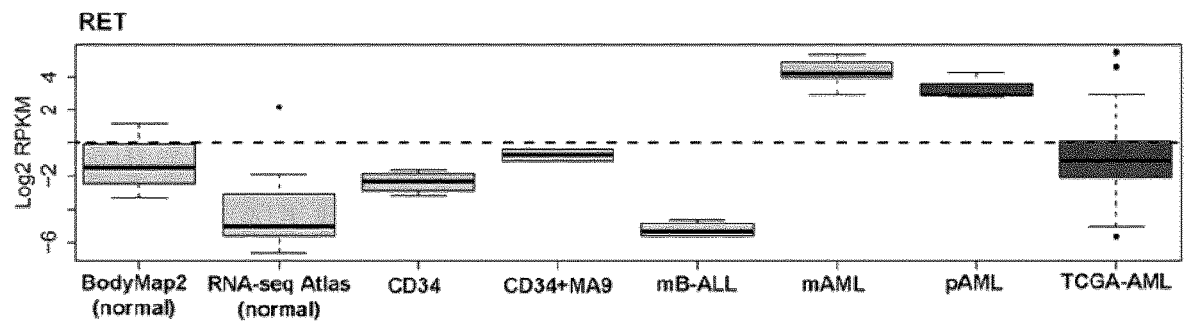
FIGS. 4A to D show boxplots of candidate gene expression in a variety of tissues. The expression of a subset of candidate genes is shown above (FIG. 4A=RET.
Figure 4B:
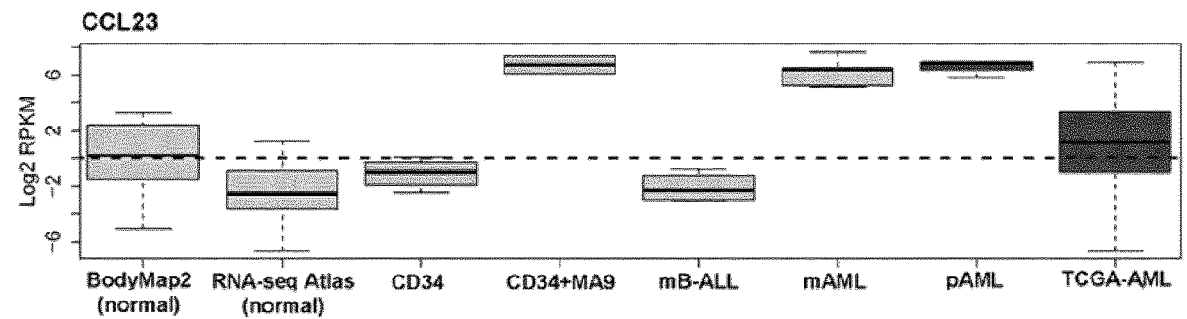
Figure 4C:
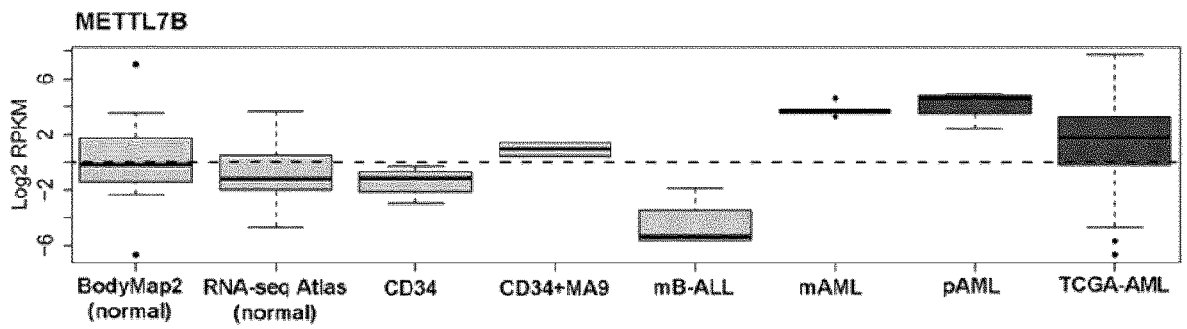
Figure 4D:
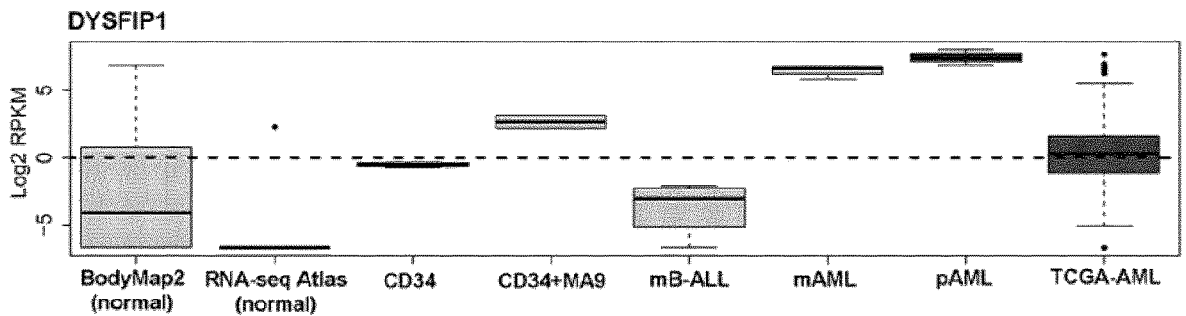

The bioinformatic analysis methods for next generation DNA sequencing involves mapping paired reads back to the human reference genome (hg19) using CASAVA (Ver 1.8) to generate normalized gene expression values (RPKM) as well as quantitative reports of reads spanning exon junctions. The process used for the subsequent data filtering is shown in FIG. 3. After generation of expression data for the model leukemia samples, these were compared to the initial cord blood samples as well as the CD34$^+$ cells containing the MLL-AF9 transgene. Potential AML candidate genes were retained if their expression was absent (RPKM<1) in both averaged CD34$^+$ cells as well as model B-ALL samples from the same donors in addition to monocytes from other donors. The resulting genes whose expression was restricted to the MLL-AF9 transduced CD34$^+$ cells and model AML cells were then compared to the pediatric AML samples and the publically accessible TCGA AML data. Genes whose expression was also high in the pediatric AML samples (RPKM value>3) were retained. Publically available RNA-seq data for gene expression in normal tissues (Illumina™ BodyMap2) was downloaded and used to exclude candidate genes which had expression (RPKM>1) in white blood cells (WBC). Published data for Illumina™ beadchip gene expression in 8 defined subpopulations of hematopoietic cells (6 donors per sub-population) was also downloaded and used to examine expression levels of candidate genes (Table 6). Based on above filters, 39 genes were identified based on their expression in model AML and pediatric samples, but not in CD34, monocyte or model B-ALL samples (Table 1), and 12 genes were identified based on their expression in model B-ALL, AML and pediatric samples, but not in CD34 and monocyte samples (Table 2).

TABLE 6

Expression values of candidate and control genes in HaemeAtlas normal blood cell data (PMID: 19228925)

Table 6A: lineage and control High/Low genes

| Cell type | Lineage | | | | |
|---|---|---|---|---|---|
| | CD2 | CD3E | CD4 | CD8A | CD14 |
| Ave_Th_lymphocyte | 13312 | 3046 | 1657 | 380 | 135 |
| Ave_Tc_lymphocyte | 12384 | 2916 | 332 | 13103 | 2040 |
| Ave_monocyte | 283 | 144 | 2723 | 124 | 30916 |
| Ave_B_lymphocyte | 172 | 152 | 211 | 132 | 1067 |
| Ave_NK | 9595 | 1331 | 291 | 6010 | 1810 |
| Ave_granulocyte | 131 | 143 | 224 | 118 | 9092 |
| Ave_megakaryocyte | 218 | 163 | 236 | 123 | 176 |
| Ave_erthroblast | 145 | 157 | 176 | 130 | 144 |

| Cell type | Lineage | | | |
|---|---|---|---|---|
| | CD33 | CD34 | CD40 | CD44 |
| Ave_Th_lymphocyte | 138 | 110 | 142 | 22057 |
| Ave_Tc_lymphocyte | 472 | 108 | 164 | 16460 |
| Ave_monocyte | 6713 | 107 | 392 | 26193 |
| Ave_B_lymphocyte | 273 | 111 | 1407 | 10285 |
| Ave_NK | 546 | 111 | 176 | 13069 |
| Ave_granulocyte | 559 | 112 | 110 | 5839 |
| Ave_megakaryocyte | 545 | 135 | 581 | 1075 |
| Ave_erthroblast | 337 | 135 | 145 | 4488 |

| Cell type | High | | Low | |
|---|---|---|---|---|
| | RPL38 | RPS16 | MYOD1 | SRY |
| Ave_Th_lymphocyte | 51392 | 44902 | 132 | 118 |
| Ave_Tc_lymphocyte | 52973 | 48409 | 128 | 117 |
| Ave_monocyte | 50441 | 49107 | 125 | 117 |
| Ave_B_lymphocyte | 53146 | 49129 | 132 | 119 |
| Ave_NK | 48866 | 47280 | 133 | 122 |
| Ave_granulocyte | 13609 | 11166 | 129 | 119 |
| Ave_megakaryocyte | 59121 | 58986 | 161 | 144 |
| Ave_erthroblast | 58080 | 54478 | 155 | 154 |

Table 6B: MLL-AF9 AML Candidates

| Cell type | MLL-AF9 AML Candidates | | | | |
|---|---|---|---|---|---|
| | CCL23 | DEFB1 | SCUBE1 | TRPM4 | PHACTR3 |
| Ave_Th_lymphocyte | 109 | 102 | 112 | 126 | 117 |
| Ave_Tc_lymphocyte | 122 | 105 | 116 | 172 | 117 |
| Ave_monocyte | 126 | 115 | 115 | 662 | 116 |
| Ave_B_lymphocyte | 114 | 108 | 118 | 142 | 121 |
| Ave_NK | 142 | 108 | 114 | 157 | 126 |
| Ave_granulocyte | 1583 | 104 | 113 | 141 | 117 |
| Ave_megakaryocyte | 332 | 141 | 127 | 659 | 157 |
| Ave_erthroblast | 169 | 132 | 135 | 189 | 138 |

| Cell type | MLL-AF9 AML Candidates | | | | |
|---|---|---|---|---|---|
| | METTL7B | RET | AGT | SAGE1 | ARTN |
| Ave_Th_lymphocyte | 135 | 116 | 152 | 104 | 124 |
| Ave_Tc_lymphocyte | 150 | 117 | 154 | 108 | 122 |
| Ave_monocyte | 158 | 122 | 152 | 104 | 124 |
| Ave_B_lymphocyte | 164 | 122 | 162 | 109 | 129 |
| Ave_NK | 147 | 121 | 158 | 109 | 124 |
| Ave_granulocyte | 154 | 119 | 160 | 104 | 122 |
| Ave_megakaryocyte | 166 | 158 | 175 | 119 | 143 |
| Ave_erthroblast | 151 | 137 | 177 | 126 | 141 |

TABLE 6-continued

Expression values of candidate and control genes in HaemeAtlas normal blood cell data (PMID: 19228925)

| | MLL-AF9 AML Candidates | | | | |
|---|---|---|---|---|---|
| Cell type | IL31RA | CD276 | SYT17 | DES | CABP4 |
| Ave_Th_lymphocyte | 128 | 130 | 133 | 122 | 228 |
| Ave_Tc_lymphocyte | 136 | 130 | 129 | 124 | 185 |
| Ave_monocyte | 133 | 133 | 139 | 131 | 138 |
| Ave_B_lymphocyte | 139 | 133 | 307 | 126 | 290 |
| Ave_NK | 133 | 136 | 131 | 128 | 259 |
| Ave_granulocyte | 141 | 131 | 130 | 121 | 124 |
| Ave_megakaryocyte | 136 | 166 | 152 | 153 | 151 |
| Ave_erthroblast | 143 | 168 | 151 | 211 | 145 |

| | MLL-AF9 AML Candidates | | | | |
|---|---|---|---|---|---|
| Cell type | LPL | MT1G | C17orf55 | FAM70A | RUFY4 |
| Ave_Th_lymphocyte | 122 | 179 | 97 | 128 | 155 |
| Ave_Tc_lymphocyte | 123 | 164 | 98 | 149 | 170 |
| Ave_monocyte | 200 | 179 | 143 | 133 | 157 |
| Ave_B_lymphocyte | 120 | 130 | 99 | 136 | 162 |
| Ave_NK | 116 | 152 | 99 | 159 | 166 |
| Ave_granulocyte | 123 | 141 | 97 | 133 | 170 |
| Ave_megakaryocyte | 144 | 145 | 112 | 142 | 175 |
| Ave_erthroblast | 141 | 176 | 111 | 138 | 172 |

| | MLL-AF9 AML Candidates | | | | |
|---|---|---|---|---|---|
| Cell type | NRG4 | KIF26B | NAV3 | ITGA7 | NXF3 |
| Ave_Th_lymphocyte | 126 | 147 | 117 | 134 | 118 |
| Ave_Tc_lymphocyte | 132 | 151 | 117 | 135 | 122 |
| Ave_monocyte | 138 | 149 | 119 | 149 | 120 |
| Ave_B_lymphocyte | 136 | 153 | 123 | 140 | 123 |
| Ave_NK | 129 | 151 | 122 | 138 | 130 |
| Ave_granulocyte | 128 | 153 | 132 | 143 | 132 |
| Ave_megakaryocyte | 143 | 149 | 137 | 156 | 128 |
| Ave_erthroblast | 150 | 167 | 135 | 149 | 145 |

| | MLL-AF9 AML Candidates | | | | |
|---|---|---|---|---|---|
| Cell type | PDZD7 | CLSTN2 | SLC22A20 | GIPR | DYSFIP1 |
| Ave_Th_lymphocyte | 115 | 97 | NA | 140 | NA |
| Ave_Tc_lymphocyte | 121 | 93 | NA | 150 | NA |
| Ave_monocyte | 118 | 91 | NA | 143 | NA |
| Ave_B_lymphocyte | 118 | 101 | NA | 146 | NA |
| Ave_NK | 122 | 98 | NA | 146 | NA |
| Ave_granulocyte | 118 | 97 | NA | 152 | NA |
| Ave_megakaryocyte | 138 | 124 | NA | 158 | NA |
| Ave_erthroblast | 136 | 120 | NA | 155 | NA |

| | MLL-AF9 AML Candidates | | | | |
|---|---|---|---|---|---|
| Cell type | BCL2L10 | LOC100289656 | KCNN2 | LOC728606 | TGM5 |
| Ave_Th_lymphocyte | 111 | NA | 113 | NA | 96 |
| Ave_Tc_lymphocyte | 113 | NA | 118 | NA | 100 |
| Ave_monocyte | 110 | NA | 116 | NA | 98 |
| Ave_B_lymphocyte | 120 | NA | 122 | NA | 101 |
| Ave_NK | 109 | NA | 114 | NA | 103 |
| Ave_granulocyte | 112 | NA | 118 | NA | 100 |
| Ave_megakaryocyte | 135 | NA | 141 | NA | 134 |
| Ave_erthroblast | 127 | NA | 137 | NA | 116 |

| | MLL-AF9 AML Candidates | | | |
|---|---|---|---|---|
| Cell type | PITX1 | TMEM105 | CCDC144NL | HOXA11 |
| Ave_Th_lymphocyte | 146 | 96 | NA | 114 |
| Ave_Tc_lymphocyte | 163 | 101 | NA | 118 |
| Ave_monocyte | 154 | 107 | NA | 114 |
| Ave_B_lymphocyte | 156 | 110 | NA | 124 |
| Ave_NK | 156 | 103 | NA | 117 |
| Ave_granulocyte | 164 | 104 | NA | 118 |

TABLE 6-continued

Expression values of candidate and control genes in HaemeAtlas normal blood cell data (PMID: 19228925)

| | | | | |
|---|---|---|---|---|
| Ave_megakaryocyte | 160 | 115 | NA | 130 |
| Ave_erthroblast | 163 | 125 | NA | 137 |

Table 6C: MLL-AF9 Leukemia Candidates

| Cell type | MLL-AF9 Leukemia Candidates | | | |
|---|---|---|---|---|
| | CD70 | LAMP5 | THBS4 | LOC84989 |
| Ave_Th_lymphocyte | 319 | 121 | 110 | NA |
| Ave_Tc_lymphocyte | 344 | 134 | 110 | NA |
| Ave_monocyte | 155 | 205 | 111 | NA |
| Ave_B_lymphocyte | 476 | 180 | 112 | NA |
| Ave_NK | 244 | 167 | 111 | NA |
| Ave_granulocyte | 159 | 121 | 233 | NA |
| Ave_megakaryocyte | 169 | 261 | 135 | NA |
| Ave_erthroblast | 6768 | 134 | 145 | NA |

| Cell type | MLL-AF9 Leukemia Candidates | | | |
|---|---|---|---|---|
| | CTGF | ECM1 | CDKN2A | PENK |
| Ave_Th_lymphocyte | 134 | 122 | 113 | 102 |
| Ave_Tc_lymphocyte | 132 | 126 | 114 | 104 |
| Ave_monocyte | 133 | 124 | 100 | 109 |
| Ave_B_lymphocyte | 269 | 130 | 114 | 113 |
| Ave_NK | 134 | 131 | 114 | 105 |
| Ave_granulocyte | 129 | 134 | 101 | 103 |
| Ave_megakaryocyte | 335 | 232 | 129 | 119 |
| Ave_erthroblast | 159 | 161 | 151 | 123 |

| Cell type | MLL-AF9 Leukemia Candidates | | | |
|---|---|---|---|---|
| | GAS2L3 | PHLDA3 | SERINC2 | GPM6B |
| Ave_Th_lymphocyte | 133 | 125 | 161 | 125 |
| Ave_Tc_lymphocyte | 130 | 121 | 163 | 140 |
| Ave_monocyte | 153 | 106 | 253 | 120 |
| Ave_B_lymphocyte | 135 | 118 | 172 | 155 |
| Ave_NK | 134 | 122 | 169 | 139 |
| Ave_granulocyte | 129 | 114 | 201 | 127 |
| Ave_megakaryocyte | 208 | 194 | 181 | 134 |
| Ave_erthroblast | 347 | 436 | 229 | 147 |

Table 6A shows expression of various lineage markers on the 8 blood cell types, genes known to be highly expressed (ribosomal genes; "high") or lowly expressed (transcription factors expressed in other tissues, "low") are shown to demonstrate extremes of the expression range. Table 6B shows the expression of a subset of our candidates in normal blood cells, demonstrating that many of these have no expression, indicating their utility as biomarkers for leukemia.

Figure 2A:
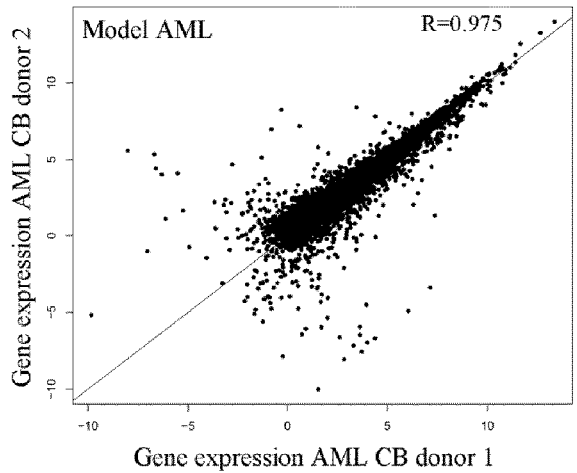
FIGS. 2A and B show that the gene expression pattern is highly reproducible in model leukemias between donors.
Figure 2B:
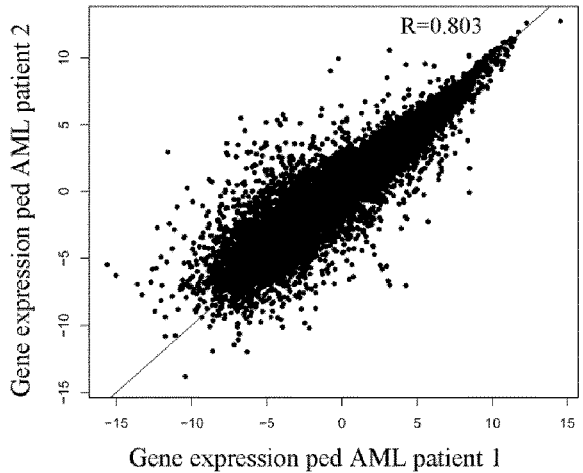
FIG. 2B shows gene expression data from two pediatric MA9-AML patients from the BCLQ, sequenced and analyzed using the same methodology. Pearson correlation (R) for pairs of AMLs is shown in upper right of FIGS. 2A and B.

Example 2: Identification and Utility of Candidate Genes as t(9:11) AML Biomarkers The data presented in FIGS. 2A and 2B show that the gene expression patterns measured by RNA-seq sequencing are highly reproducible in two AMLs derived from two independent cord blood donors (FIG. 2A) as well as in two pediatric MA9-AML patients.

Figure 5:
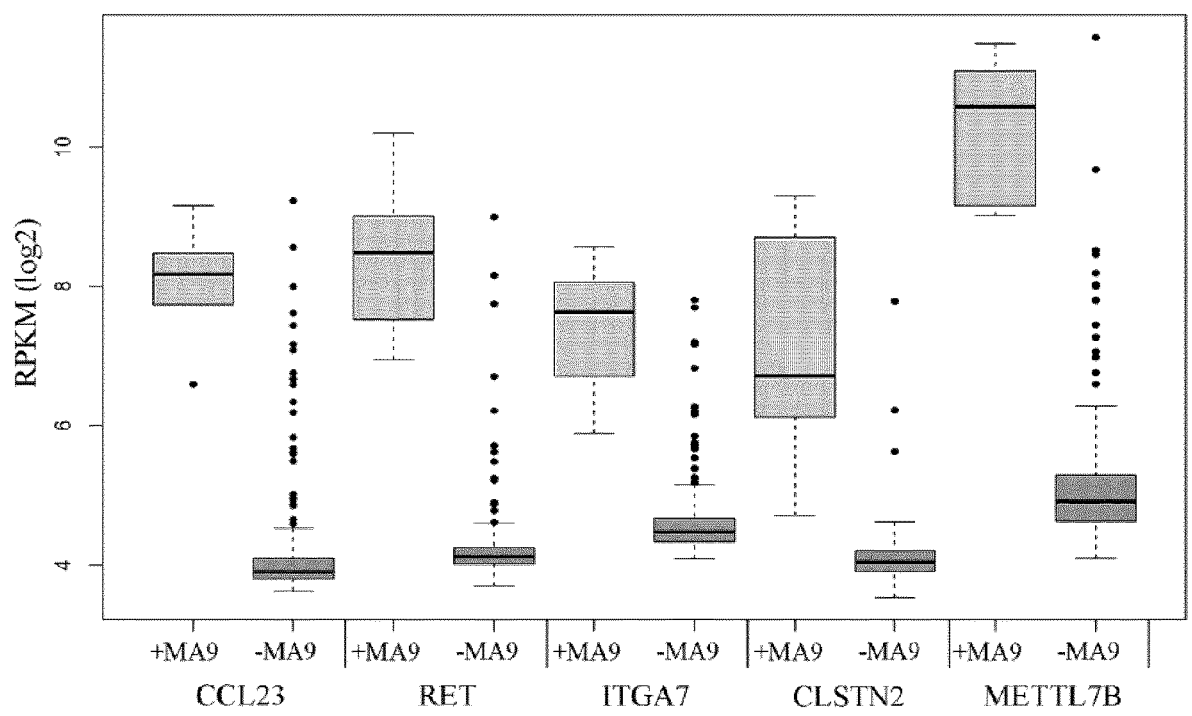
FIG. 5 shows the expression of candidate genes in 180 hematopoietic cell lines. Data from the cell line encyclopedia project (Broad Institute) shows that candidate genes exhibit expression specific to MA9 containing cell lines (+MA9; n=6) compared to non-MA9 cell lines (−MA9; n=174)
Figure 6:
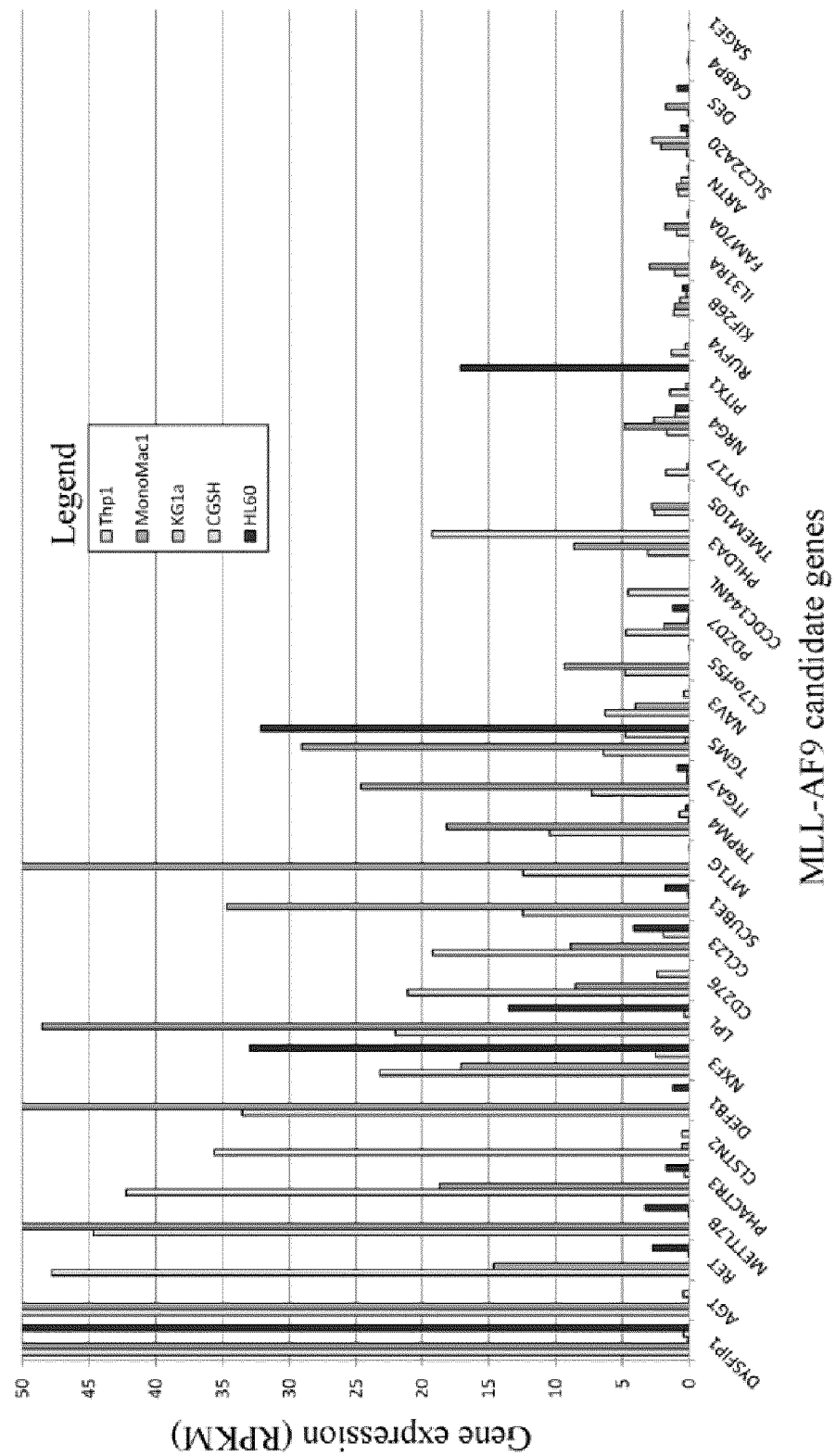
FIG. 6 shows RNA-seq data for candidate genes. RNA-seq was performed on 5 hematopoietic cell lines, 2 with MA9 translocations, THP-1 (left bars) and MonoMac1 (second bars), and 3 without MA9 translocations, KG1a (third, middle bars), CG-SH (fourth bars) and HL60 (last bars). A majority of candidate genes identified in model and patient MA9-AMLs show an expression pattern that is also specific to MA9-cell lines.

Using the approach described above (FIGS. 1 and 3), 39 genes that have characteristics which make them useful as biomarkers for t(9:11) leukemias and in some instances for other potential leukemia types were identified (Table 1). All of these genes have been demonstrated to be expressed in the t(9:11) AML leukemia model as well as multiple pediatric AML samples which also contain the (9:11) translocation. The results depicted in FIGS. 4A-D and Tables 1-2 show that the candidate genes typically exhibit no or low expression in several independent sources of normal tissues, which reduces the risk of adverse diagnostic potential. Importantly, a large sample (>45) of normal blood cells also shows that most of these genes are not expressed in the majority of the cell types examined (Table 5). This is a very desirable trait for the monitoring a hematological malignancy since it also significantly reduces the likelihood of false positives from any potential diagnostic test. To further validate the AML specific and t(9:11) specific expression pattern of the candidate genes, RNA-seq was performed on 5 AML cell lines, 2 of which (THP-1 and MonoMac1) contains a (9:11) (MA9) translocation (FIG. 6). Interestingly, a number of the candidate's genes are not expressed in any cell line other than THP-1 and MonoMac1, further evidencing that the expression of these genes is specific to MLL-AF9 translocations. In addition, almost all of the candidate genes show a higher expression level in THP-1 and/or MonoMac1 cells compared to the 3 other cell lines. Also, FIG. 5 shows that candidate genes CCL23, RET, ITGA7, CLSTN2 and METTL7B exhibit expression specific to MA9 containing cell lines relative to non-MA9 cell lines. Taken together, these results indicate that the biomarkers do have an AML specific and largely t(9:11) restricted expression pattern ideally suited for diagnostic or therapeutic use.

Figure 7A:
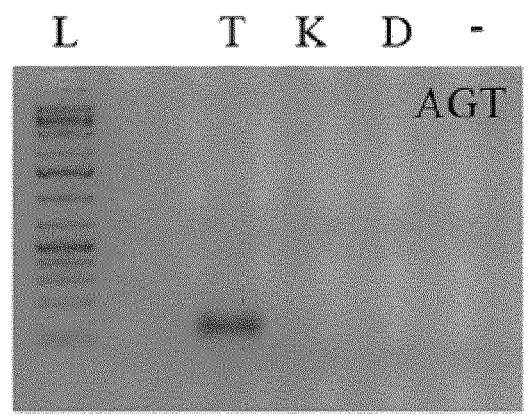
FIGS. 7A and B show RT-PCR data for candidate genes—100 bp product size.
Figure 7B:
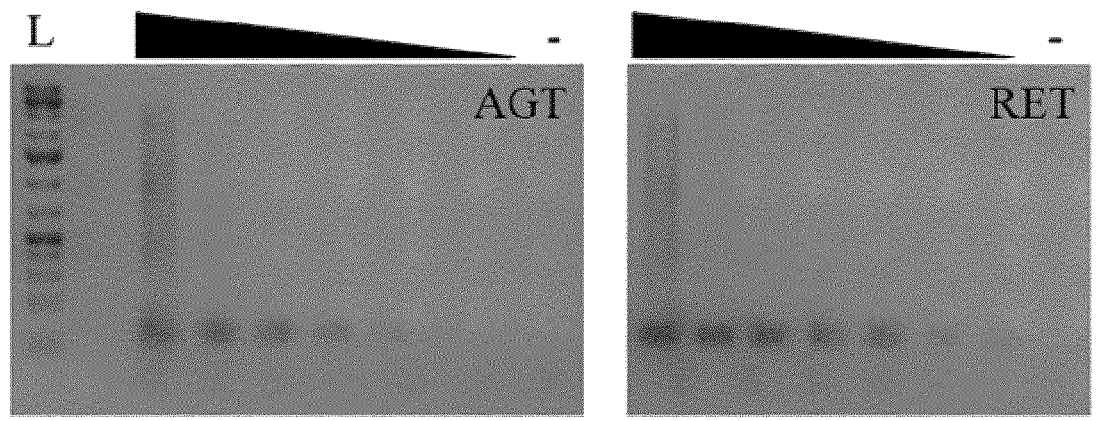
FIG. 7B shows RT-PCR data for AGT (left panel) and RET (right panel) from THP-1 and KG1a cDNA in different ratios to test sensitivity. First lane corresponds to a 10:1 THP-1:KG1a ratio, and each subsequent lane corresponds to a 10-fold dilution of THP-1 cDNA added (e.g., $2^{nd}$ line is 1:1, $7^{th}$ lane is 1:$10^5$, and $8^{th}$ line is KG1a cDNA only). 35 cycles were used for all PCRs, L=ladder.
Figure 8A:
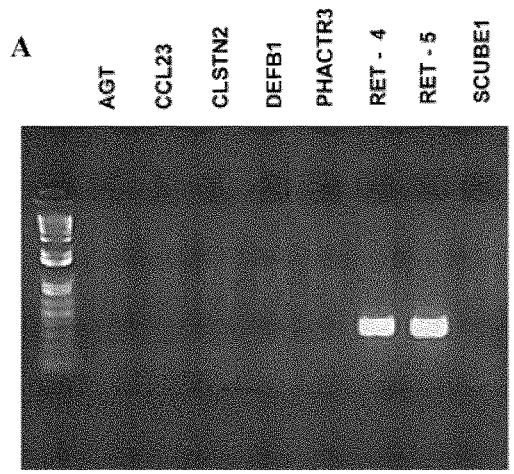
FIGS. 8A to D show RT-PCR data for candidate genes—300 bp product size.
Figure 8B:
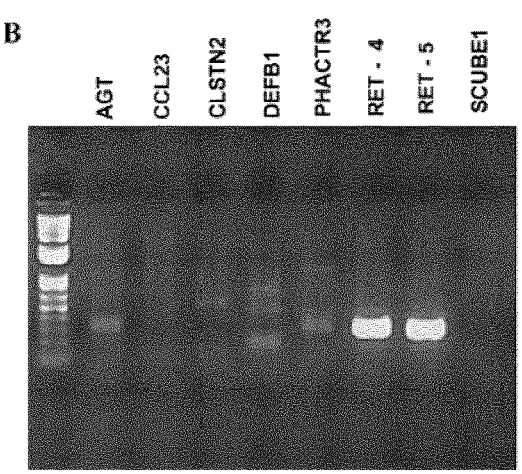
Figure 8C:
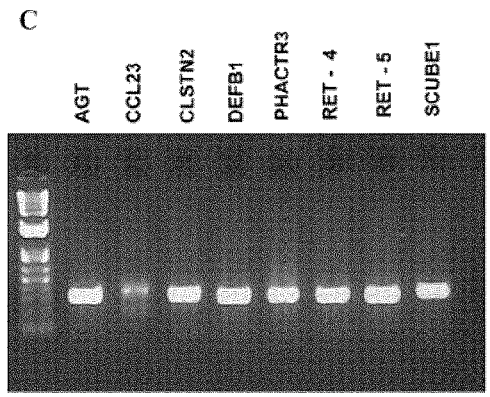
Figure 8D:
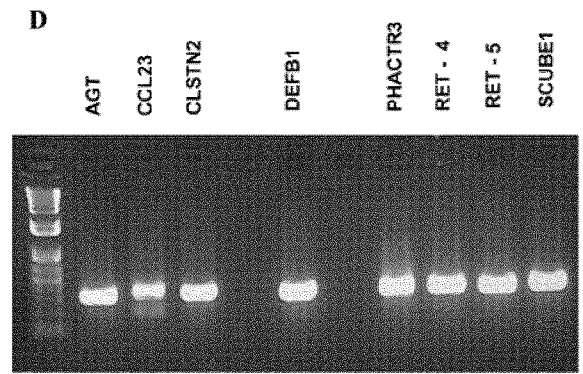
Figure 9A:
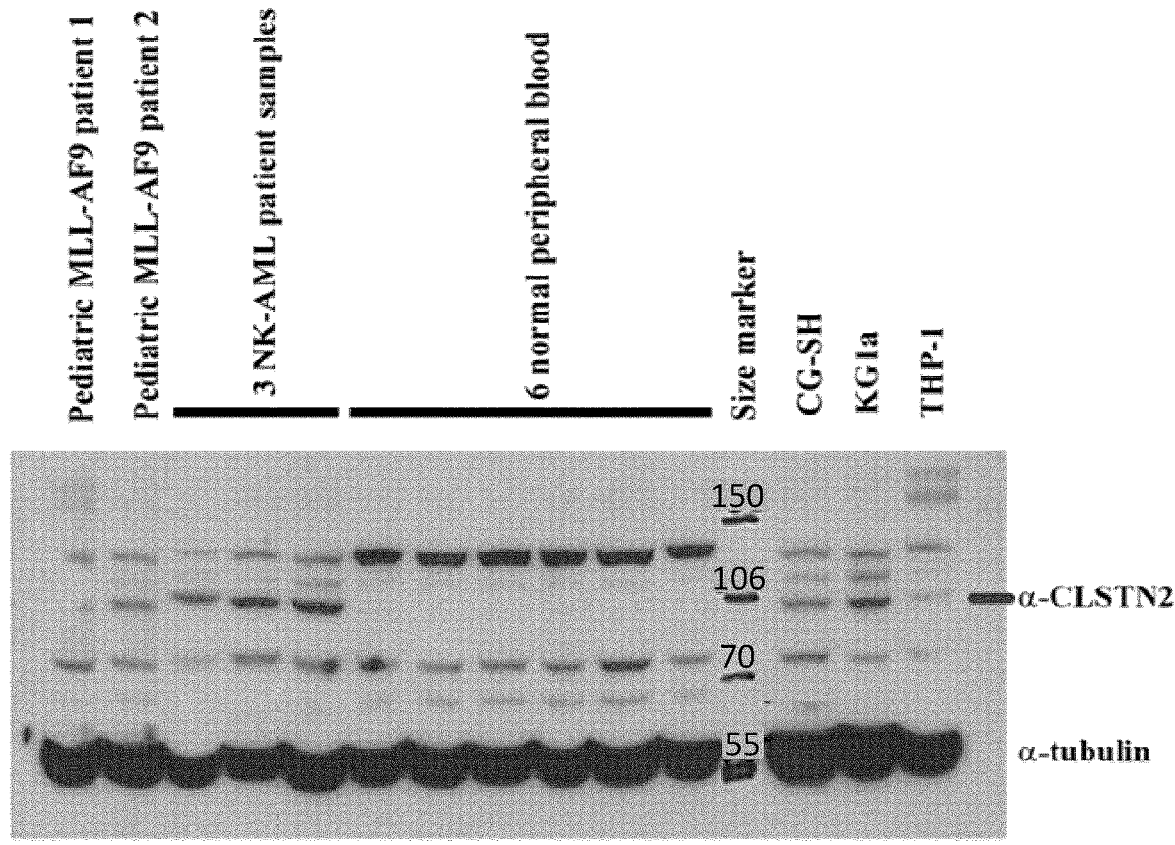
FIGS. 9A and B show Western blots of two MLL-AF9 AML candidate genes, namely CLSTN2 (FIG. 9A) and RET (FIG. 9B). Protein extracts were prepared from 2 pediatric AML patient samples (both containing MLL-AF9 translocations), 3 normal karyotype adult AML patient samples, peripheral blood from 6 normal healthy volunteers, and 3 leukemia cell lines (CG-SH, KG1a and THP-1, with only THP-1 containing an MLL-AF9 translocation). The Western blot in FIG. 9A shows that only leukemic cells or cell lines exhibit a band of the expected size for CLSTN2; additional bands are believed to be products of non-specific binding.
Figure 9B:
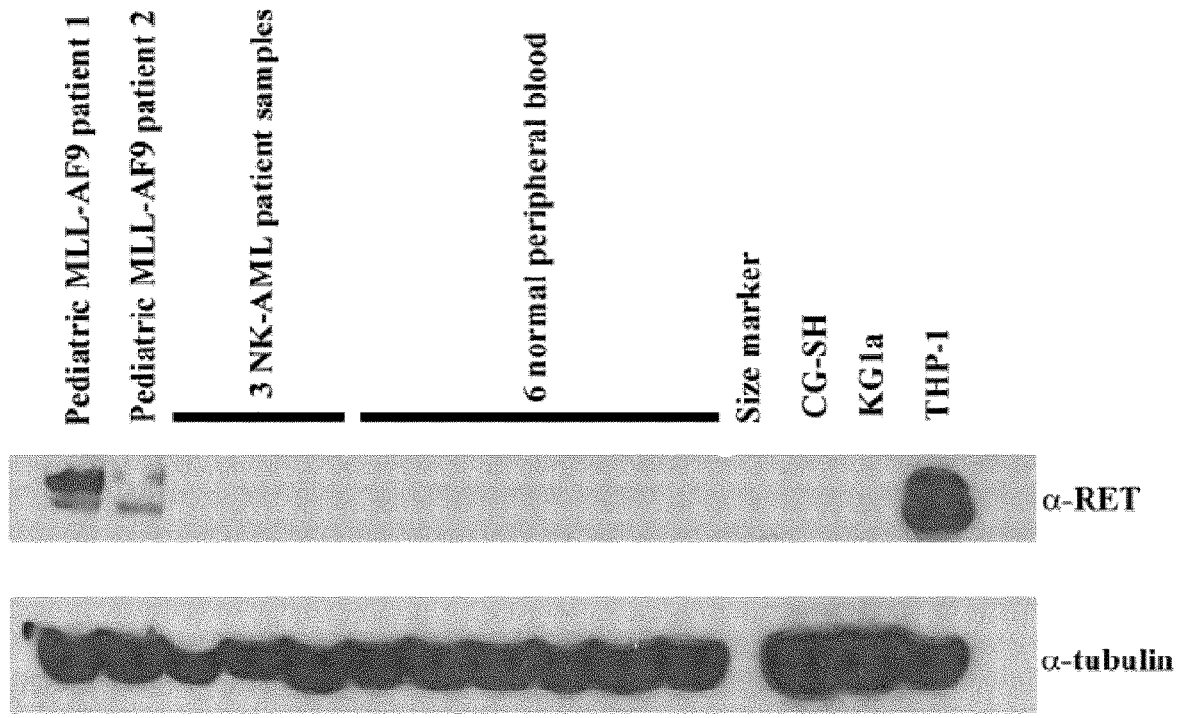
FIG. 9B shows that the presence of RET can only be detected in AML cells (from patients or lines) which contain an MLL-AF9 translocation. In both panels, Western blot against alpha-tubulin is shown as a loading control.

The results depicted in FIGS. 7A and B and FIGS. 8A to D demonstrate the detection by RT-PCR of candidate genes AGT, CCL23, CLSTN2, DEFB1, PHACTR3, RET and SCUBE1 in cells containing an MLL-AF9 translocation (THP-1), but not in those that do not contain an MLL-AF9 translocation (KG1a), further evidencing the ability of the candidate genes to specifically identify MLL-AF9 translocations. The results depicted in FIG. 9A show the detection by Western blot of CLSTN2 in leukemic cells and leukemic cell lines, but not in normal peripheral blood cells. FIG. 9B shows that the detection of RET by Western blot is restricted to cells from pediatric MLL-AF9 patients and the MA9 containing cell line THP-1.

Figure 10:
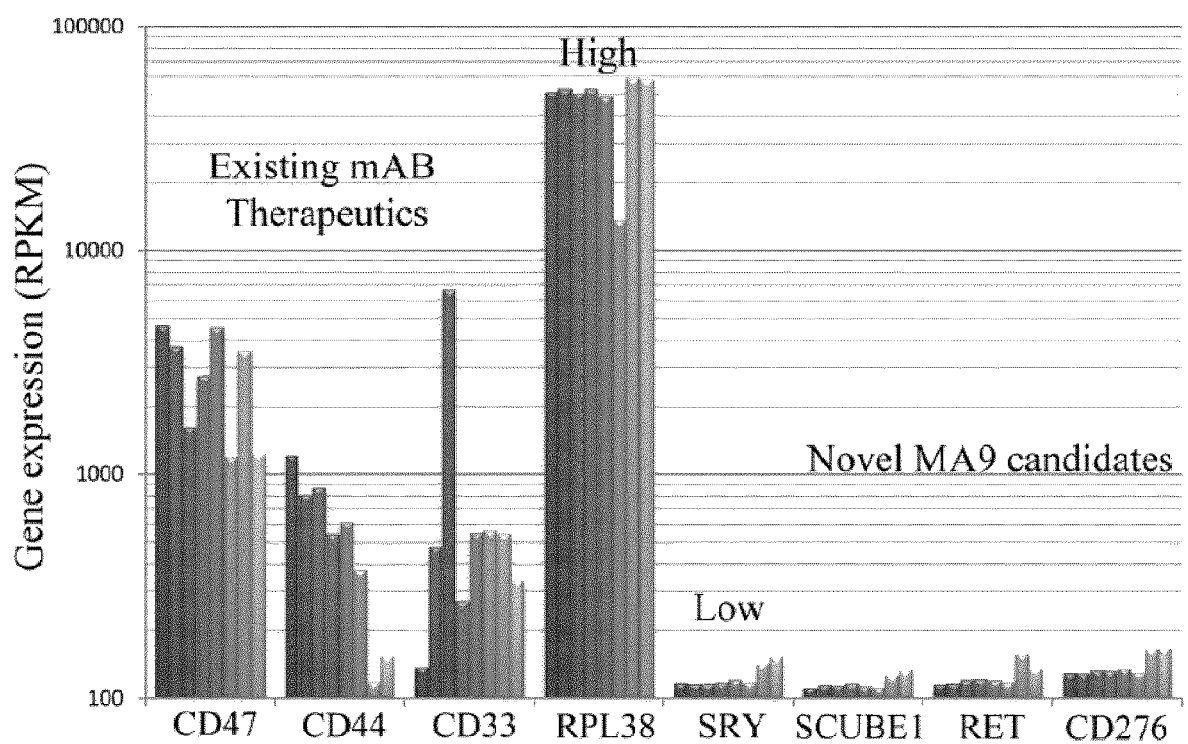
FIG. 10 shows gene expression levels of 3 current AML antibody-based therapeutic targets (CD47, CD44, CD33) in 8 normal blood cell types. Control genes demonstrating high (RPL38) and low (SRY) gene expression are shown ($4^{th}$ and $5^{th}$ sets). Last three sets show 3 MLL-AF9 genes uncovered through comparison of RNA-seq data from the model AML and pediatric AML samples described herein. Blood cell expression data is from HaemAtlas project and shows average gene expression for 8 healthy donors for 8 cell types, namely T helper cells ($1^{st}$ bars), cytotoxic T cells ($2^{nd}$ bars), Monocytes ($3^{rd}$ bars), B cells ($4^{th}$ bars), NK cells ($5^{th}$ bars), granulocytes ($6^{th}$ bars), megakaryocytes ($7^{th}$ bars), and erythroblasts ($8^{th}$ bars). Novel candidate MLL-AF9 (MA9) genes have little or no expression in normal blood cells, which provides evidence that antibody-based therapies targeting these genes could result in lower levels of side-effects.

The expression of candidate genes SCUBE1, RET and CD276 in 8 normal blood cell types was compared to that of 3 current AML therapeutic targets (CD47, CD44, CD33). The data depicted in FIG. 10 shows that candidate MLL-AF9 (MA9) genes SCUBE1, RET and CD276 are expressed at lower levels in normal blood cells relative to CD47, CD44 and CD33, providing evidence that these genes are more specific to MLL-AF9 relative to current AML therapeutic targets and thus that antibody-based therapies targeting these proteins could result in lower levels of side-effects.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", an and the include corresponding plural references unless the context clearly dictates otherwise.

What is claimed is:

1. A method for treating acute myeloid leukemia (AML) involving translocation of the mixed-lineage leukemia (MLL) gene in a subject, said method comprising administering to said subject an effective amount of a monoclonal antibody or an antigen-binding fragment thereof that binds to one or more of the following proteins: RET and CD70.

2. The method of claim 1, wherein the monoclonal antibody or antigen-binding fragment thereof binds to RET.

3. The method of claim 1, wherein the monoclonal antibody or antigen-binding fragment thereof binds to CD70.

* * * * *